(12) United States Patent
Swanson

(10) Patent No.: US 12,661,173 B2
(45) Date of Patent: Jun. 23, 2026

(54) HIGH-VOLTAGE PULSE ABLATION SYSTEMS AND METHODS

(71) Applicant: AtriCure, Inc., Mason, OH (US)

(72) Inventor: David K. Swanson, Campbell, CA (US)

(73) Assignee: AtriCure, Inc., Mason, OH (US)

( * ) Notice: Subject to any disclaimer, the term of this patent is extended or adjusted under 35 U.S.C. 154(b) by 312 days.

(21) Appl. No.: 18/335,226

(22) Filed: Jun. 15, 2023

(65) Prior Publication Data

US 2023/0320773 A1    Oct. 12, 2023

Related U.S. Application Data

(60) Continuation of application No. 16/906,979, filed on Jun. 19, 2020, now Pat. No. 11,918,271, which is a
(Continued)

(51) Int. Cl.
    *A61B 18/14*          (2006.01)
    *A61B 18/08*          (2006.01)
    (Continued)

(52) U.S. Cl.
    CPC ............ *A61B 18/085* (2013.01); *A61B 18/08* (2013.01); *A61B 18/10* (2013.01); *A61B 18/1206* (2013.01); *A61B 2018/00351* (2013.01); *A61B 2018/00363* (2013.01); *A61B 2018/00392* (2013.01); *A61B 2018/00577* (2013.01);
    (Continued)

(58) Field of Classification Search
    CPC .............. A61B 18/085; A61B 18/1442; A61B 18/1445; A61B 2018/1253; A61B 2018/126; A61B 2018/1452; A61B 2018/0072; A61B 2018/00732; A61B 2018/1455; A61B 2018/0063; A61B 2018/00636; A61B 2018/00642; A61B 2018/00351; A61B 2018/00363; A61B 2018/00392; A61B 2018/00577; A61B 2018/00613; A61B 2018/00654; A61B 2018/00702; A61B 2018/00589;
    (Continued)

(56) References Cited

U.S. PATENT DOCUMENTS 7,742,811 B2* 6/2010 Schroeppel ............ A61N 1/403
                                                          607/3
8,353,907 B2* 1/2013 Winkler ................. A61B 18/18
                                                          606/41
(Continued)

*Primary Examiner* — Thomas A Giuliani
(74) *Attorney, Agent, or Firm* — Dorton & Willis LLP; Ryan Willis

(57)          ABSTRACT

A tissue treatment system configured to ablate a tissue, the system comprising: (a) a clamp assembly comprising a first jaw mechanism and a second jaw mechanism configured to receive and compress a tissue therebetween; (b) a first electrode disposed on the first jaw mechanism and configured to contact the tissue; and (c) a second electrode disposed on the second jaw mechanism and configured to contact the tissue, where the first electrode and the second electrode are configured so that at least one of an ablation energy output of the first electrode and an ablation energy output of the second electrode is automatically adjusted to accommodate variable tissue thicknesses between the first electrode and the second electrode.

10 Claims, 12 Drawing Sheets

Related U.S. Application Data division of application No. 14/745,136, filed on Jun. 19, 2015, now Pat. No. 10,722,286, which is a continuation of application No. 13/149,687, filed on May 31, 2011, now Pat. No. 9,072,518.

(51) Int. Cl.

| | |
|---|---|
| *A61B 18/10* | (2006.01) |
| *A61B 18/12* | (2006.01) |
| *A61B 18/00* | (2006.01) |
| *A61B 18/06* | (2006.01) |
| *A61B 18/18* | (2006.01) |
| *A61B 18/20* | (2006.01) |
| *A61N 7/02* | (2006.01) |

(52) U.S. Cl.
CPC .............. *A61B 2018/00613* (2013.01); *A61B 2018/00654* (2013.01); *A61B 2018/00702* (2013.01); *A61B 2018/00797* (2013.01); *A61B 18/06* (2013.01); *A61B 2018/145* (2013.01); *A61B 18/1815* (2013.01); *A61B 18/20* (2013.01); *A61N 2007/025* (2013.01)

(58) Field of Classification Search
CPC ........... A61B 2018/00595; A61B 2018/00607; A61B 2018/00619
USPC ...... 606/41, 42, 45, 48–52; 607/98, 99, 101, 607/113, 115, 116
See application file for complete search history.

(56) References Cited

U.S. PATENT DOCUMENTS

| | | | | |
|---|---|---|---|---|
| 2005/0203504 A1* | 9/2005 | Wham | ............... | A61B 18/1442 606/34 |
| 2008/0172048 A1* | 7/2008 | Martin | ............... | A61B 18/1442 601/3 |
| 2010/0023004 A1* | 1/2010 | Francischelli | ..... | A61B 18/1492 606/41 |
| 2011/0098694 A1* | 4/2011 | Long | .................. | A61B 18/1492 606/41 |
| 2012/0220998 A1* | 8/2012 | Long | .................. | A61B 18/1206 606/41 |

* cited by examiner

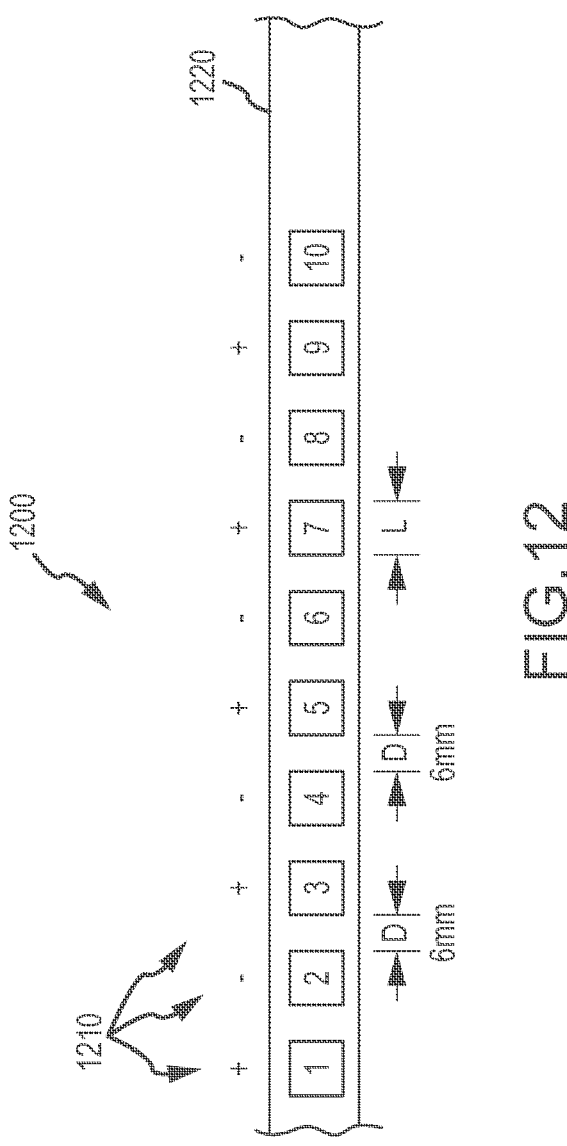
F I G. 12

HIGH-VOLTAGE PULSE ABLATION SYSTEMS AND METHODS

CROSS-REFERENCES TO RELATED APPLICATIONS

This application is a continuation of U.S. Nonprovisional patent application Ser. No. 16/906,979, filed Jun. 19, 2020, now U.S. Pat. No. 11,918,271, which is a divisional of U.S. Nonprovisional patent application Ser. No. 14/745,136, filed Jun. 19, 2015, now U.S. Pat. No. 10,722,286, which is a continuation of U.S. Nonprovisional patent application Ser. No. 13/149,687, filed May 31, 2011, now U.S. Pat. No. 9,072,518, the entire content of which is incorporated herein by reference for all purposes. This application is related to U.S. Pat. Nos. 6,369,465, 6,428,537, and 6,679,269, the disclosures of which are incorporated herein by reference.

BACKGROUND OF THE INVENTION

Embodiments of the present invention related generally to the field of medical devices and methods, and in particular to therapeutic modalities involving tissue ablation or lesion formation.

Atrial fibrillation (AF) can refer to a heart beat rhythm disorder (or "cardiac arrhythmia") in which the upper chambers of the heart known as the atria quiver rapidly instead of beating in a steady rhythm. This rapid quivering reduces the heart's ability to properly function as a pump. AF is a common clinical condition, and presents a substantial medical issue to aging populations. AF is costly to health systems, and can cause complications such as thrombo-embolism, heart failure, electrical and structural remodeling of the heart, and even death. Relatedly, AF typically increases the risk of acquiring a number of potentially deadly complications, including thrombo-embolic stroke, dilated cardiomyopathy, and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures. The likelihood of developing AF increases dramatically as people age; the disorder is found in about 1% of the adult population as a whole, and in about 6% of those over age 60. By age 80, about 9% of people (one in 11) will have AF. According to a recent statistical analysis, the prevalence of AF in the U.S. will more than double by the year 2050, as the proportion of elderly increases. A recent study called The Anticoagulation and Risk Factors in Atrial Fibrillation (ATRIA) study, published in the Spring of 2001 in the Journal of the American Medical Association (JAMA), found that 2.3 million U.S. adults currently have AF and this number is likely to increase over the next 50 years to more than 5.6 million, more than half of whom will be age 80 or over.

As the prevalence of AF increases, so will the number of people who develop debilitating or life-threatening complications, such as stroke. According to Framingham Heart Study data, the stroke rate in AF patients increases from about 3%/year of those aged 50-59 to more than 7%/year of those aged 80 and over. AF is responsible for up to 35% of the strokes that occur in people older than age 85. Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be under-prescribed for AF. Despite the fact that warfarin reduces stroke risk by 60% or more, only 40% of patients age 65-74 and 20% of patients over age 80 take the medication, and probably fewer than half are on the correct dosage. Patient compliance with pharmacological intervention such as warfarin is problematic, and the drug requires vigilant blood monitoring to reduce the risk of bleeding complications.

More recently, the focus has shifted toward surgical or catheter ablation options to treat or effect a cure for AF. The ablation techniques for producing lines of electrical isolation are now replacing the so-called Maze procedure. The Maze procedure uses a set of transmural surgical incisions on the atria to create fibrous scars in a prescribed pattern. This procedure was found to be highly efficacious but was associated with a high morbidly rate. The more recent approach of making lines of scar tissue with modern ablation technology has enabled the electrophysiologist or cardiac surgeon to create the lines of scar tissue more safely. Ideally, re-entrant circuits that perpetuate AF can be interrupted by the connected lines of scar tissue, and the goal of achieving normal sinus rhythm in the heart may be achieved.

Electrophysiologists often classify AF by the "three Ps": paroxysmal, persistent, or permanent. Paroxysmal AF, typically characterized by sporadic, usually self-limiting episodes lasting less than 48 hours, is usually the most amenable to treatment, while persistent or permanent AF can be much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is often characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Triggers for intermittent AF and drivers for permanent AF can be located at various places on the heart, such as the atria. For example, where triggers or drivers are located near the pulmonary veins, it follows that treatment may involve electrical isolation of the pulmonary veins. Technologies designed to isolate the pulmonary veins or ablate specific pulmonary foci appear to be very promising and are the focus of much of the current research in catheter-based ablation techniques.

There are many instances where it is beneficial to perform a therapeutic intervention in a patient, using a system that is inserted within the patient's body. One exemplary therapeutic intervention involves the formation of therapeutic lesions in the patient's heart tissue to treat cardiac conditions such as atrial fibrillation, atrial flutter, and arrhythmia. Therapeutic lesions may also be used to treat conditions in other regions of the body including, but not limited to, the prostate, liver, brain, gall bladder, uterus, and other solid organs. Typically, the lesions are formed by ablating tissue with one or more electrodes. For example, certain cardiac surgical procedures involve administering ablative energy to the cardiac tissue in an attempt to create a transmural lesion on the tissue. Although cardiac ablation devices and methods are currently available and provide real benefits to patients in need thereof, many advances may still be made to provide improved devices and methods for creating lesions in cardiac tissue to treat AF and other arrhythmias. Embodiments of the present invention provide solutions to at least some of these outstanding needs.

BRIEF SUMMARY OF THE INVENTION

Embodiments of the present invention provide systems and methods for administering minimally invasive stand-alone atrial fibrillation therapy using bipolar clamping technology. Embodiments further encompass very effective ablation technologies that provide the flexibility of linear monopolar devices with the effectiveness of bipolar clamping devices. In some cases, systems and methods encompass the use of high-voltage pulses as a non-thermal means of ablating tissue. Embodiments are well suited for use with unipolar and bipolar ablation techniques, and encompass treatments involving box lesions and conduction block, as well as the administration of tissue stunning protocols.

High-voltage pulses applied by the electrode eventually kills or ablates the tissue to form a lesion. Depending on the procedure, a variety of different electrophysiology devices may be used to position one or more electrodes at the target location. Electrodes can be connected to power supply lines and, in some instances, the power to the electrodes can be controlled on an electrode-by-electrode basis. Examples of electrophysiology devices include catheters, surgical probes, and clamps. The ablation energy output of individual ablation electrodes can be automatically adjusted so as to accommodate for variable tissue thicknesses.

In one aspect, embodiments of the present invention encompass methods of administering an ablation treatment to a patient that include compressing a portion of a patient target tissue with a bipolar clamp assembly, where the clamp assembly includes a first jaw having a first electrode mechanism and a first face and a second jaw having a second electrode mechanism and a second face, such that the first jaw face and the second jaw face are separated by less than about 5 mm. Methods can also include applying a high voltage pulse regimen to the tissue with the bipolar clamp ablation assembly. The pulse regimen can provide or include a plurality of 500 1000 volt pulses each having a duration of between about 0.02 msec and about 0.1 msec. The pulses can be delivered at a frequency having a pulse number within a range from about 5 to about 50 pulses discharged over a time interval within a range from about 1 to about 60 seconds. In some instances, the patient tissue includes a plurality of myocardial cells, and the ablation treatment is sufficient to kill the plurality of myocardial cells between the jaw faces. In some instances, the patient tissue includes a plurality of myocardial cells, and the ablation treatment is sufficient to irreversible damage the plurality of myocardial cells. In some instances, the portion of patient tissue includes a strip of tissue between the first jaw face and the second jaw face, and the ablation treatment is sufficient to create a lesion within the strip of tissue, such that the lesion has a maximum width disposed midway between the first jaw face and the second jaw face. Optionally, the first jaw face may include a first electrode having a width of about 2 mm and the second jaw face may include a second electrode having a width of about 2 mm, and the maximum width of the lesion can be about 10 mm or less.

In another aspect, embodiments of the present invention encompass methods of administering an ablation treatment to a patient that include placing a return pad at a location on the patient's skin, and placing an ablation assembly at a patient target tissue, where the ablation assembly includes a first electrode mechanism and a second electrode mechanism. Methods may also include applying a high voltage pulse regimen to the tissue between the first and second electrode mechanism with the ablation assembly. The pulse regimen may include or provide a plurality of 1000 2000 volt pulses each having a duration of between about 0.02 msec and about 0.1 msec. The pulses can be delivered at a frequency having a pulse number within a range from about 5 to about 50 pulses discharged over a time interval within a range from about 1 to about 60 seconds. In some cases, the patient tissue includes a plurality of myocardial cells, and the ablation treatment is sufficient to kill at least a portion of the plurality of myocardial cells located within about 5 mm of either of the first electrode mechanism or the second electrode mechanism. In some cases, the patient tissue includes a plurality of myocardial cells, and the ablation treatment is sufficient to irreversible damage the plurality of myocardial cells. In some cases, the high voltage pulse regimen includes or provides multiple volt pulses each having an amplitude of about 1000 volts and a pulse width of about 0.05 msec. Optionally, the high voltage pulse regimen can be sufficient to ablate the target tissue to a depth of about 5 mm. In some cases, the high voltage pulse regimen includes or provides multiple volt pulses each having an amplitude of about 2000 volts and a pulse width of about 0.05 msec. Optionally, the high voltage pulse regimen can be sufficient to ablate the target tissue to a depth of about 10 mm. In some cases, the tissue has a thickness of about 10 mm and the ablation treatment is sufficient to create a lesion within the tissue, where the lesion has a substantially semicircular cross-section. In some instances, the tissue has a thickness and the ablation treatment is sufficient to create a lesion within the tissue, the lesion having a width of about twice the tissue thickness. In some instances, the tissue includes an atrial wall tissue having a thickness of about 4 mm and the ablation treatment is sufficient to create a lesion within the tissue, the lesion having a width of about 8 mm. Optionally, the application of the high voltage pulse regimen may result in little or no cellular damage in the patient's skin near the return pad. In some cases, the application of the high voltage pulse regimen results in a voltage gradient of about 10V/cm or lower at the patient's skin near the return pad.

In another aspect, embodiments of the present invention encompass methods of administering an ablation treatment to a patient that include placing a return pad at a location on the patient's skin, and placing an ablation assembly at a patient target tissue. The ablation assembly can include a first electrode mechanism and a second electrode mechanism, where the first and second electrode mechanisms are spaced more than about 2 cm apart. Methods may also involve applying a high voltage pulse regimen to the tissue between the first and second electrode mechanisms with the ablation assembly. The pulse regimen can include or provide a plurality of 1500 3000 volt pulses each having a duration of between about 0.02 msec and about 0.1 msec. In some cases, the patient tissue includes a plurality of myocardial cells, and the ablation treatment is sufficient to kill at least a portion of the plurality of myocardial cells located within about 5 mm of each of the first electrode mechanism and the second electrode mechanism. In some cases, the pulses are delivered at a frequency having a pulse number within a range from about 5 to about 50 pulses discharged over a time interval within a range from about 1 to about 60 seconds. In some cases, the patient tissue includes a plurality of myocardial cells, and the ablation treatment is sufficient to irreversible damage the plurality of myocardial cells. Optionally, the high voltage pulse regimen may include or provide multiple volt pulses each having an amplitude of about 1500 volts and a pulse width of about 0.05 msec. In some instances, the high voltage pulse regimen is sufficient to ablate the target tissue to a depth of about 5 mm. In some instances, the high voltage pulse regimen includes or provides multiple volt pulses each having an amplitude of about 3000 volts and a pulse width of about 0.05 msec. Optionally, the high voltage pulse regimen can be sufficient to ablate the target tissue to a depth of about 10 mm. In some cases, the tissue has a thickness of about 10 mm and the ablation treatment is sufficient to create a lesion within the tissue, the lesion comprising a substantially semicircular cross-section. In some cases, the tissue has a thickness and the ablation treatment is sufficient to create a lesion within the tissue, the lesion having a width of about twice the tissue thickness. In some cases, the tissue includes an atrial wall tissue having a thickness of about 4 mm and the ablation treatment is sufficient to create a lesion within the tissue, the lesion having a width of about 8 mm.

In yet another aspect, embodiments of the present invention encompass methods of administering an ablation treatment to a patient that include placing an ablation assembly at a patient target tissue, where the ablation assembly includes a first electrode mechanism having a first electrode with a first polarity and a second electrode mechanism having a second electrode with a second polarity opposite the first polarity. The first and second electrode mechanisms can be spaced more than about 2 cm apart. Methods may also include applying a high voltage pulse regimen to the tissue between the first and second electrode mechanisms with the ablation assembly, where the pulse regimen includes or provides a plurality of 1000 2000 volt pulses each having a duration of between about 0.02 msec and about 0.1 msec. In some instances, the first electrode and the second electrode are similarly sized. In some instances, the second electrode mechanism includes a plurality of second electrodes with a second polarity opposite the first polarity, where each of the second electrodes spaced more than about 2 cm from the first electrode. In some cases, the patient tissue includes a plurality of myocardial cells, and the ablation treatment is sufficient to kill at least a portion of the plurality of myocardial cells located within about 5 mm of the first electrode mechanism. In some cases, the pulses are delivered at a frequency having a pulse number within a range from about 5 to about 50 pulses discharged over a time interval within a range from about 1 to about 60 seconds. In some cases, the patient tissue includes a plurality of myocardial cells, and the ablation treatment is sufficient to irreversible damage the plurality of myocardial cells. In some cases, the high voltage pulse regimen includes or provides multiple volt pulses each having an amplitude of about 1000 volts and a pulse width of about 0.05 msec. Optionally, the high voltage pulse regimen can be sufficient to ablate the target tissue to a depth of about 5 mm at the first electrode mechanism. In some cases, the high voltage pulse regimen includes or provides multiple volt pulses each having an amplitude of about 2000 volts and a pulse width of about 0.05 msec. Optionally, the high voltage pulse regimen can be sufficient to ablate the target tissue to a depth of about 10 mm at the first electrode mechanism. In some instances, the tissue has a thickness of about 10 mm and the ablation treatment is sufficient to create a lesion within the tissue, where the lesion has a substantially semicircular cross-section. In some instances, the tissue has a thickness and the ablation treatment is sufficient to create a lesion within the tissue, where the lesion has a width of about twice the tissue thickness. In some instances, the tissue includes an atrial wall tissue having a thickness of about 4 mm and the ablation treatment is sufficient to create a lesion within the tissue, the lesion having a width of about 8 mm. Optionally, application of the high voltage pulse regimen can result in a lesion having a first depth at the first electrode mechanism and a second depth at the second electrode mechanism, where the second lesion depth is less than the first lesion depth. Some methods may include placing a return pad at a location on the patient's skin.

In still a further aspect, embodiments of the present invention encompass methods of administering an ablation treatment to a patient that include placing a return pad at a location on the patient's skin, and placing an ablation assembly at a patient target tissue. The ablation assembly can include a first electrode mechanism and a second electrode mechanism, where the first and second electrode mechanisms are spaced at a distance from each other within a range from about 4 mm to about 10 mm. In some cases, the patient target tissue has a thickness, and the first and second electrode mechanisms are spaced at a distance from each other approximately equal to the target tissue thickness. In some cases, the first electrode mechanism has a first length and the second electrode mechanism has a second length, where each of the first and second lengths are within a range from about 4 mm to about 20 mm. Some methods may include applying a high voltage pulse regimen to the tissue between the first and second electrode mechanisms with the ablation assembly, where the pulse regimen includes or provides a plurality of 1500 3000 volt pulses each having a duration of between about 0.02 msec and about 0.1 msec. In some cases, the patient tissue includes a plurality of myocardial cells, and the ablation treatment is sufficient to kill at least a portion of the plurality of myocardial cells located within about 5 mm of each of the first electrode mechanism and the second electrode mechanism. In some cases, the first electrode mechanism can be configured to deliver voltage at a first polarity, and the second electrode mechanism can be configured to deliver voltage at a second polarity that is opposite the first polarity. Sources of energy can be configured to provide such voltages to the electrodes. In some cases, the patient target tissue includes an atrial wall. Optionally, the atrial wall can have a thickness of about 4 mm and the first and second electrode mechanisms can present or define an edge to edge separation distance of about 6 mm. In some cases, the pulses are delivered at a frequency having a pulse number within a range from about 5 to about 50 pulses discharged over a time interval within a range from about 1 to about 60 seconds. According to some embodiments, the patient tissue includes a plurality of myocardial cells, and the ablation treatment is sufficient to irreversible damage the plurality of myocardial cells. In some instances, the high voltage pulse regimen includes or provides multiple volt pulses each having an amplitude of about 1500 volts and a pulse width of about 0.05 msec. Optionally, the high voltage pulse regimen can be sufficient to ablate the target tissue to a depth of about 5 mm at each of the first electrode mechanism and the second electrode mechanism. In some instances, the high voltage pulse regimen includes multiple volt pulses each having an amplitude of about 3000 volts and a pulse width of about 0.05 msec. In some instances, the high voltage pulse regimen is sufficient to ablate the target tissue to a depth of about 10 mm at each of the first electrode mechanism and the second electrode mechanism. In some instances, the tissue has a thickness of about 10 mm and the ablation treatment is sufficient to create a lesion within the tissue, the lesion comprising a substantially semicircular cross-section. In some instances, the tissue has a thickness and the ablation treatment is sufficient to create a lesion within the tissue, the lesion having a width of about twice the tissue thickness. In some instances, the tissue includes an atrial wall tissue having a thickness of about 4 mm and the ablation treatment is sufficient to create a lesion within the tissue, the lesion having a width of about 8 mm.

The above described and many other features and attendant advantages of embodiments of the present invention will become apparent and further understood by reference to the following detailed description when considered in conjunction with the accompanying drawings.

BRIEF DESCRIPTION OF THE DRAWINGS

FIG. 12 illustrates aspects of a tissue treatment system according to embodiments of the present invention.

DETAILED DESCRIPTION OF THE INVENTION

Figure 1A:
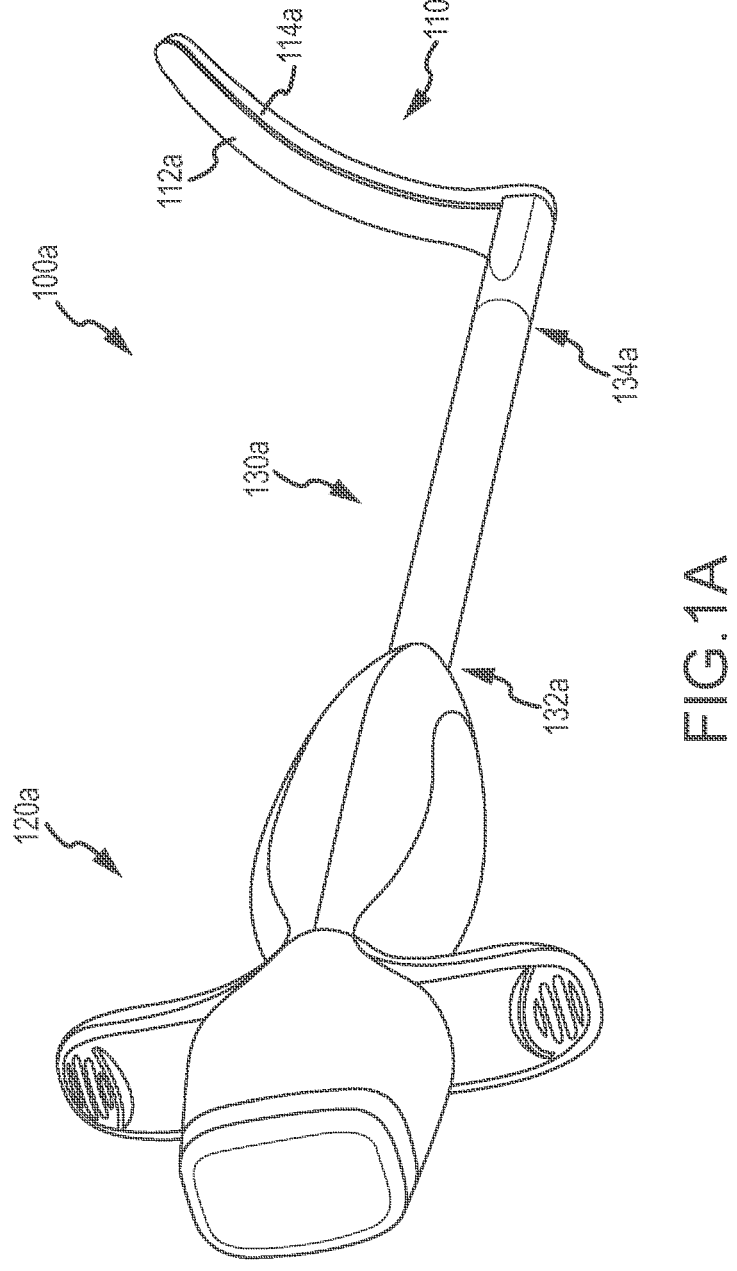
FIGS. 1A and 1B illustrates aspects of a tissue treatment system according to embodiments of the present invention.

Surgical probes which can be used to create lesions often include a handle, a relatively short shaft that is from 4 inches to 18 inches in length and either rigid or relatively stiff, and a distal section that is from 1 inch to 10 inches in length and either malleable or somewhat flexible. One or more electrodes are carried by the distal section. Surgical probes are used in epicardial and endocardial procedures, including open heart procedures and minimally invasive procedures where access to the heart is obtained via a thoracotomy, thoracostomy or median sternotomy. Exemplary surgical probes are disclosed in U.S. Pat. No. 6,142,994, the content of which is incorporated herein by reference.

Clamps, which have a pair of opposable clamp members that may be used to hold a bodily structure or a portion thereof, are used in many types surgical procedures. Lesion-creating electrodes have also been secured to certain types of clamps. Examples of clamps which carry lesion creating electrodes are discussed in U.S. Provisional Patent Application No. 61/288,031 filed Dec. 18, 2009, U.S. Pat. No. 6,142,994, and U.S. Patent Publication Nos. 2003/0158549, 2004/0059325, and 2004/024175, the contents of which are incorporated herein by reference. Such clamps can be useful when the physician intends to position electrodes on opposite sides of a body structure in a bipolar arrangement.

Many currently available ablation devices typically use temperature extremes to create lesions. Most systems apply energy to the target tissue to heat it, and wherever the tissue temperature exceeds about 50° C., myocytes are killed. If cryotherapy probes are used, myocytes are killed when local temperatures reach temperatures below about −40° C. Whichever ablative device is used, the affected electrically responsive tissue is replaced by non-responsive tissue (scar tissue) which blocks conduction. Thus, energy-based surgical ablative treatments for the treatment of atrial fibrillation attempt to provide lines of conduction block in atrial tissue without the need to cut the tissue and sew it back together. The effective ablative treatments create permanent conduction block by the same mechanism as the cut- and sew technique: a scar is eventually formed that forms a line of block across the entire thickness of the atrial wall.

For heat-generating ablation technologies, the size and shape of the lesion created can by defined by the volume of the tissue heated to 50° C. and above. Expressed in another way, the 50° C. isotherm forms the boundary of the lesion created by such technologies. For normothermic patients, this corresponds to a 13° C. increase in local tissue temperature. For safety reasons, typically none of the heated tissue should be heated to above 100° C., since the steam so created can disrupt the tissue, or even cause an atrial wall perforation. This constraint limits both the power levels and power application times for the energy heating the tissue. In summary, tissue should generally be heated by at least 13° C. to be effective, but safety concerns limit heating to 63° C. for normothermic patients. Since safety is an important design constraint for ablation devices, this relatively narrow therapeutically effective window can result in ablation designs that are ineffective under some operating conditions. One design strategy that addresses this issue is to use local surface temperature to control energy delivery to the tissue. This strategy can be especially effective for ablation technology that creates the hottest tissue temperatures near the tissue surface. This approach enables more aggressive applications of energy to heat the tissues while avoiding potentially dangerous overheating situations. The superior results with the technology using RF heating with temperature control tend to validate that approach to ablation device design.

For many heat-generating ablation technologies, the size and shape of the lesion created can be determined by both the direct heating pattern of the tissue by the ablating device and by passive heat conduction from the hotter regions of the directly heated tissue to cooler less strongly heated regions. Heat conduction usually results in larger lesions than could be created by heat deposition patterns alone. With the exception of bipolar ablation technologies, most heat-generating technologies currently on the market have more than a 5 to 1 variation in deposited power within 2 mm of the tissue surface through which the power enters. For such technologies, lesion dimensions are typically extended well beyond 2 mm by heat conduction from tissues heated above 50° C. Although lesion growth by heat conduction is generally a much slower process than the process of heating tissue directly by tissue absorption of the applied energy, heat conduction can result in a lesion volume more than 10 times larger than would occur by heat deposition alone as long as energy is applied long enough. However, lesion sizes may be limited when heat is actively removed into the blood stream. The convective removal of heat at the atrial endocardium can result in a thin region of sub-endocardial myocardium remaining below 50° C. and thus surviving when thermal lesions are applied epicardially. For cryotherapy lesions applied to the epicardium, heat conducts from the blood pool into the tissues, resulting in sub-endocardial temperatures remaining above freezing and sparing that tissue.

Perhaps the most widely applied technology currently in use for surgical AF therapy is RF bipolar ablation. Properly designed bipolar ablation devices can achieve reliable transmural epicardial lesions that isolate pulmonary veins. However, clinical results with this type of technology often appear to produce inferior success rates for AF therapy applied to patients with non-paroxysmal AF. In many instances, the technology suffers from a limited lesion set that can be achieved off bypass and some versions of the bipolar devices do not appear to create reliable isolation of the pulmonary veins in patients, at least for single or double RF power applications. For example, three clinical papers report that on average, more than two bipolar RF ablation applications were required to achieve acute conduction block of the right pulmonary veins and more than two bipolar RF ablation applications were required to achieve conduction block in the left pulmonary veins. Embodiments of the present invention provide improved ablation systems and methods for the treatment of atrial fibrillation.

High-voltage pulses can cause dielectric breakdown of the cellular membrane, resulting in holes being created through those membranes as described in U.S. Pat. Nos. 6,369,465; 6,428,537; and 6,679,269, the contents of which are incorporated herein by reference for all purposes. The holes can be large enough to enable proteins and even genetic material to flow out of the cells, and prior to resealing sodium and calcium can rush into the cell and potassium can rush out. Single pulses stress the cell and can result in stunning. Repeated pulses above about 500V/cm reliable kills the myocytes cells; 5-50 such pulses with pulse widths of 0.01 to 0.1 msec delivered in one minute or less can be lethal to the cells so exposed. Cells exposed to voltage gradients several fold lower than those levels will often be stunned, but will typically recover electrical and mechanical function, with those exposed to the lowest fields recovering faster.

Bipolar Clamp Technologies

For bipolar clamp ablation technologies, the system can be configured so that electrodes on the facing jaw faces are separated by less than about 5 mm after compressing the tissues between the jaw faces. In such a configuration, voltage pulses of 500-1000 volts applied between the jaw faces using pulse durations of 0.02-0.1 msec are in most instances sufficient to kill all myocardial cells between the jaw faces. When it is desired that all or substantially all of the myocardial cells be irreversibly damaged by the high voltage gradients within the targeted tissue, 10-50 pulses can be delivered over a 1 to 60 second time interval. For bipolar clamping technologies, the region of tissue subjected to the very high voltage field is usually limited to a relatively narrow strip of tissue between the jaws, with the lesion width being widest midway between the jaws. For 2 mm wide electrodes, for example, the maximum lesion width is usually 10 mm or less.

Turning now to the drawings, FIG. 1A illustrates aspects of a treatment system 100a according to embodiments of the present invention. Treatment system 100a includes a clamp assembly 110a, an actuator assembly 120a, and a coupling assembly 130a in operative association with both the clamp assembly and the actuator assembly. Clamp assembly 110a includes a first jaw mechanism 112a and a second jaw mechanism 114a. Coupling assembly 130a may include a shaft or other elongate member that allows the physician or operator to access or reach a surgical site with the clamp assembly, when the physician is holding actuator assembly 120a. Coupling assembly 130a includes a proximal end 132a and a distal end 134a. As shown here, clamp assembly 110a is coupled with distal end 134a of coupling assembly 130a, and actuator assembly 120a is coupled with proximal end 132a of coupling assembly 130a. Clamp assembly 110a is depicted in a generally closed configuration, such that first jaw mechanism 112a contacts or is situated near second jaw mechanism 114a. In some cases, a treatment system may present a disposable dedicated bipolar clamp having single-position jaws and a symmetric jaw-release on a plunger style body.

Figure 1B:
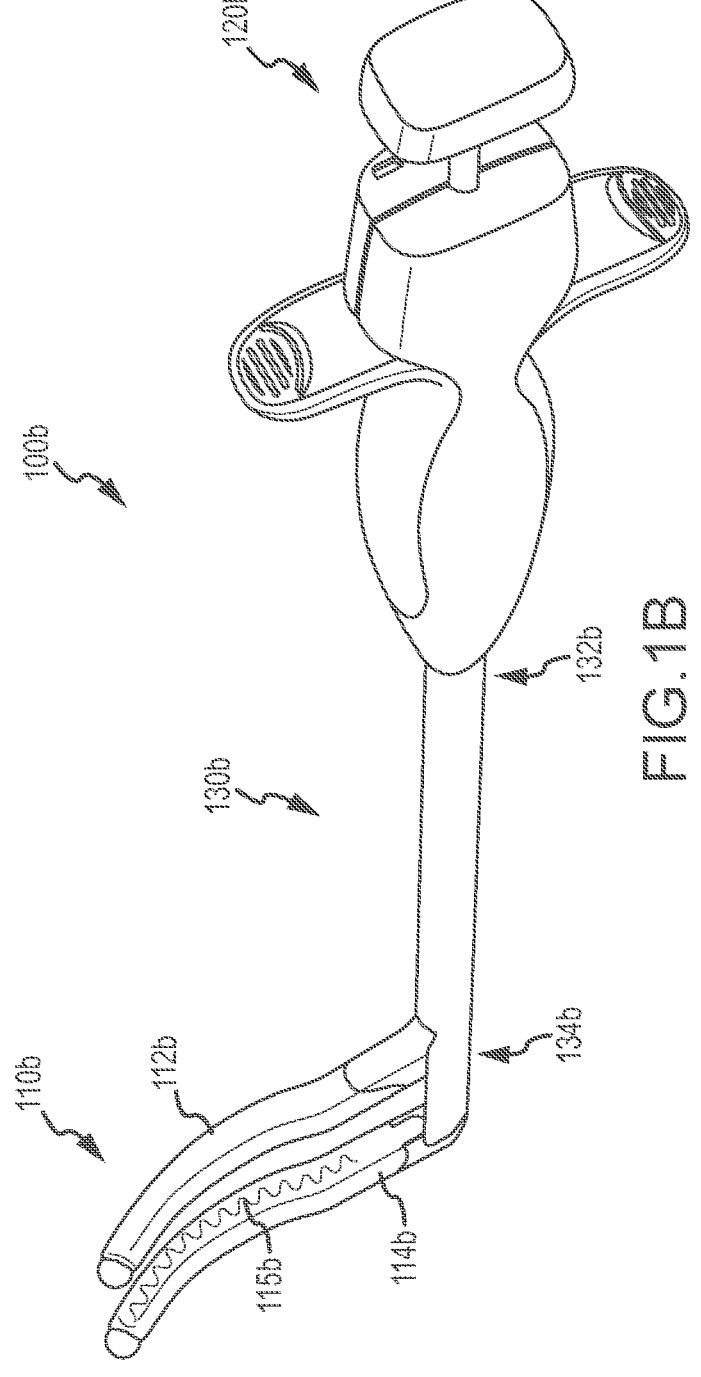

FIG. 1B illustrates aspects of a treatment system 100b according to embodiments of the present invention. Treatment system 100b includes a clamp assembly 100b, an actuator assembly 120b, and a coupling assembly 130b in operative association with both the clamp assembly and the actuator assembly. Clamp assembly 100b includes a first jaw mechanism 112b and a second jaw mechanism 114b. Coupling assembly 130b may include a shaft or other elongate member that allows the physician or operator to access or reach a surgical site with the clamp assembly, when the physician is holding actuator assembly 120b. Coupling assembly 130b includes a proximal end 132b and a distal end 134b. As shown here, clamp assembly 100b is coupled with distal end 134b of coupling assembly 130b, and actuator assembly 120b is coupled with proximal end 132b of coupling assembly 130b. Clamp assembly 100b is depicted in a generally open configuration, such that first jaw mechanism 112b does not contact or is situated at a distance from second jaw mechanism 114b. The treatment system includes a serpentine electrode or ablation member 115b disposed on second jaw mechanism 114b. The first jaw mechanism 112b includes a corresponding electrode or ablation member (not shown) that faces toward ablation member 115b. In some cases, a treatment system may present a disposable dedicated bipolar clamp having flip jaws and a symmetric jaw-release on a plunger style body.

Figure 2:
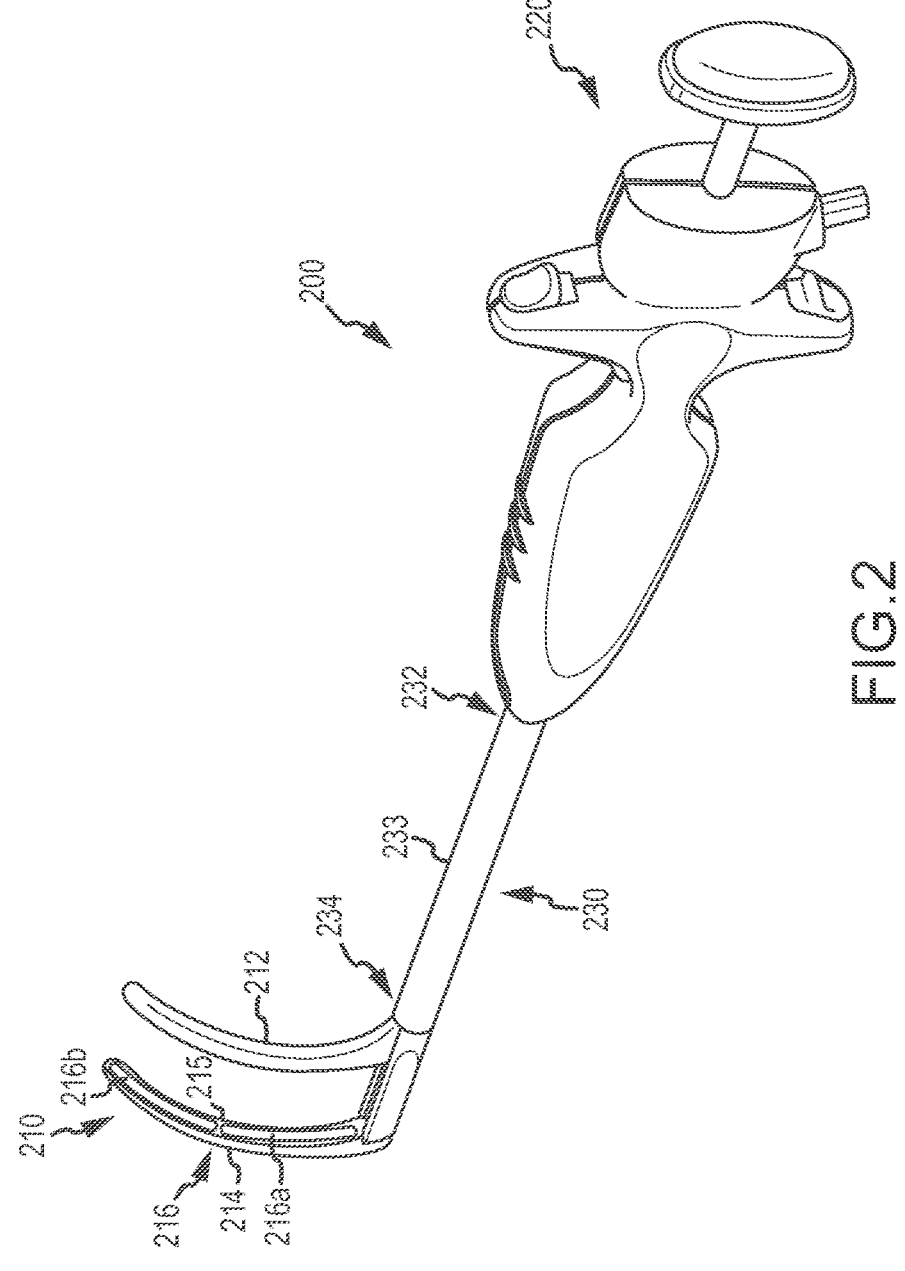
FIG. 2 illustrates aspects of a tissue treatment system according to embodiments of the present invention.

FIG. 2 shows aspects of a treatment system 200 according to embodiments of the present invention. Treatment system 200 includes a clamp assembly 210, an actuator assembly 220, and a coupling assembly 230 in operative association with both the clamp assembly and the actuator assembly. Clamp assembly 210 includes a first jaw mechanism 212 and a second jaw mechanism 214. First jaw mechanism 212 is disposed proximal to second jaw mechanism 214. The jaw mechanisms may include ablation assemblies, as well as support assemblies for holding the ablation assemblies. For example, as shown in FIG. 2, second jaw mechanism 214 includes an ablation assembly 216 having a proximal electrode 216a and a distal electrode 216b. The proximal and distal electrodes are coupled with a support assembly 215. First jaw mechanism 212 provides a similar configuration, and has one or more electrodes (not shown) that face toward electrodes 216a, 216b of distal jaw mechanism 214. In use, the surgeon or operator can use the handle or actuator assembly 220 for manipulating the treatment system, opening and closing the jaw mechanisms, activating ablation members such as electrodes 216a, 216b, and the like. Treatment system 200 can be generally configured to be introduced through a minimally invasive sheath, trocar, or incision. In some cases, treatment system 200 can be used in open surgical procedures. Coupling assembly 230 may include a shaft or other elongate member 233. In some embodiments, the shaft or elongate member may be malleable. Optionally, elongate member 233 may articulate about at least one joint and/or may be steerable for positioning the system 200. Elongate member may be made of any suitable material, such as metal, ceramic, polymers, or any combination thereof, and may be rigid along its entire length or rigid in one or more parts and flexible in one or more parts. In some embodiments, ablation assembly 216, support assembly 215, or both, are coupled with or otherwise in operative association with actuator assembly 220, optionally via coupling assembly 230. According to some embodiments, the jaw or tubular shaft elements may include a high strength material such as metal, carbon fiber, or the like.

Clamp assembly 210 may be disposed on or near a distal end 234 of coupling assembly 230, and can be generally configured to open and close to grasp epicardial or other tissue between the opposing jaw mechanisms 212, 214. As shown here, actuator assembly 220 is coupled with coupling assembly 230 via a proximal portion 232 of the coupling assembly. An ablation assembly 216 may use any suitable energy source for ablating tissue. In some embodiments, multiple ablation members may be used in a bipolar treatment technique. For example, one electrode (e.g. electrode 216a) of a bipolar ablation member may be coupled with one opposing jaw (e.g. distal jaw 214) and another corresponding electrode (not shown) may be coupled with the other opposing jaw (e.g. proximal jaw 212).

Aspects of clamp assembly 210, such as jaw mechanisms 212, 214 or ablation assemblies 216, may be shaped to contact and ablate the epicardial tissue in a pattern such as, but not limited to, a U-shaped pattern, an L-shaped pattern, a circular pattern, a nonlinear pattern, or a linear pattern. Actuator assembly 220 may enable the physician to perform one or more various system operations, such as opening and closing the jaw mechanisms 212, 214, activating an ablation assembly 216, changing an angle of orientation of a jaw mechanism 212, 214, straightening or bending a jaw mechanism 212, 214, or the like. For example, an actuator assembly may include a trigger-like actuator. Optionally, an actuator assembly may include a turnable dial.

Generally, a jaw mechanism 212, 214 may have any suitable configuration for contacting a surface of a heart, for grasping epicardial or other tissue to be ablated, for placing ablation members 216a, 216b in contact with tissue to be ablated, or for any combination thereof. As such, jaw mechanisms 212, 214 may be straight, curved, bent, or otherwise configured for contacting, grasping, or ablating tissue, or any combination thereof. In some embodiments, jaw mechanisms 212, 214 may be adjustable via actuator assembly 220, so as to allow their shapes to be bent, straightened, or the like, during a procedure. In some cases, jaw mechanisms 212, 214, can be retractable. For example, jaw mechanisms 212, 214 may be retracted within coupling assembly 230 upon one or more occasions during an operation. Retraction may help protect a patient as well as a jaw mechanism during insertion and advancement of the system within the patient.

In some embodiments, the treatment system may further include an insulation member at least partially surrounding or covering one or more the actuator assembly, coupling assembly, or clamp assembly. Such an insulation member can operate to protect body structures in the vicinity of the epicardial tissue from being ablated or damaged due to heat or electrical current. In some cases, ablation members such as electrodes 216a, 216b may be adjustable to deliver two or more varying amounts of ablative energy to two or more locations on the epicardial tissue. Various embodiments may further include at least one sensor for sensing a quantity of ablation provided by the ablation member to the tissue.

Figure 3:
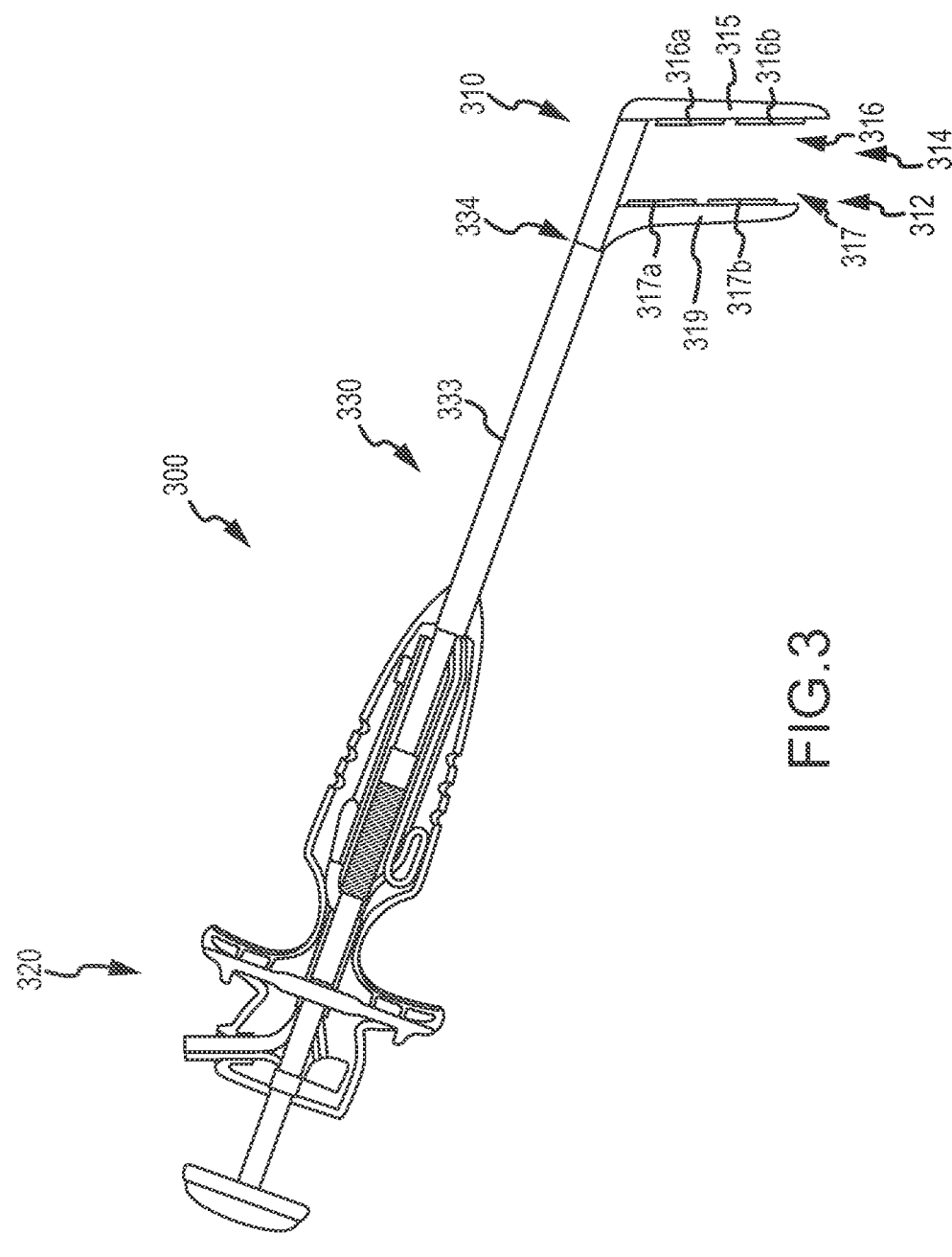
FIG. 3 illustrates aspects of a tissue treatment system according to embodiments of the present invention.

FIG. 3 shows aspects of a treatment system 300 according to embodiments of the present invention. Treatment system 300 includes a clamp assembly 310, an actuator assembly 320, and a coupling assembly 330 in operative association with both the clamp assembly and the actuator assembly. Clamp assembly 310 includes a first jaw mechanism 312 and a second jaw mechanism 314. First jaw mechanism 312 is disposed proximal to second jaw mechanism 314. The jaw mechanisms may include ablation assemblies, as well as support assemblies for holding the ablation assemblies. For example, as shown in FIG. 3, second jaw mechanism 314 includes an ablation assembly 316 having a proximal electrode 316a and a distal electrode 316b. The proximal and distal electrodes are coupled with a support assembly 315. First jaw mechanism 312 provides a similar configuration, and includes an ablation assembly 317 and a support assembly 319. The ablation assembly 317 includes a proximal electrode 317a and a distal electrode 317b that face toward electrodes 316a, 316b, respectively, of distal jaw mechanism 314. In use, the surgeon or operator can use the handle or actuator assembly 320 for manipulating the treatment system, opening and closing the jaw mechanisms, activating ablation members such as electrodes 316a, 316b, 317a, 317b, and the like. Treatment system 300 can be generally configured to be introduced through a minimally invasive sheath, trocar, or incision. In some cases, treatment system 300 can be used in open surgical procedures. Coupling assembly 330 may include a shaft or other elongate member 333. In some embodiments, the shaft or elongate member may be malleable. Optionally, elongate member 333 may articulate about at least one joint and/or may be steerable for positioning the system 300. Elongate member may be made of any suitable material, such as metal, ceramic, polymers, or any combination thereof, and may be rigid along its entire length or rigid in one or more parts and flexible in one or more parts. In some embodiments, ablation assemblies 316, 317, support assemblies 315, 319, or any combination thereof, are coupled with or otherwise in operative association with actuator assembly 320, optionally via coupling assembly 330.

Clamp assembly 310 may be disposed on or near a distal end 334 of coupling assembly 330, and can be generally configured to open and close to grasp epicardial or other tissue between the opposing jaw mechanism 312, 314. An ablation assembly 316 may use any suitable energy source for ablating tissue. In some embodiments, multiple ablation members may be used in a bipolar treatment technique. For example, one electrode (e.g electrode 316a) of a bipolar ablation member may be coupled with one opposing jaw (e.g. distal jaw 314) and another corresponding electrode (e.g. electrode 317a) may be coupled with the other opposing jaw (e.g. proximal jaw 312). Optionally, ablation assemblies may include one unipolar ablation device or any of the ablation devices described elsewhere herein.

Aspects of clamp assembly 310, such as jaw mechanisms 312, 314 or ablation assemblies 316, 317 may be shaped to contact and ablate the epicardial tissue in a pattern such as, but not limited to, a U-shaped pattern, an L-shaped pattern, a circular pattern, or a linear pattern. Actuator assembly 320 may enable the physician to perform one or more various system operations, such as opening and closing the jaw mechanisms 312, 314, activating an ablation assembly 316, 317, changing an angle of orientation of a jaw mechanism 312, 314, straightening or bending a jaw mechanism 312, 314, or the like. For example, an actuator assembly may include a trigger-like actuator. Optionally, an actuator assembly may include a turnable dial.

Generally, a jaw mechanism 312, 314 may have any suitable configuration for contacting a surface of a heart, for grasping epicardial or other tissue to be ablated, for placing ablation members 316a, 316b, 317a, 317b in contact with tissue to be ablated, or for any combination thereof. As such, jaw mechanisms 312, 314 may be straight, curved, bent, or otherwise configured for contacting, grasping, or ablating tissue, or any combination thereof. In some embodiments, jaw mechanisms 312, 314 may be adjustable via actuator assembly 320, so as to allow their shapes to be bent, straightened, or the like, during a procedure. In some cases, jaw mechanisms 312, 314, can be retractable. For example, jaw mechanisms 312, 314 may be retracted within coupling assembly 330 upon one or more occasions during an operation. Retraction may help protect a patient as well as a jaw mechanism during insertion and advancement of the system within the patient. Ablation members such as electrodes 316a, 316b, 317a, 317b, may be bipolar RF members, unipolar RF members, or any other suitable ablation devices.

In some cases, the tissue treatment systems can have a spring loaded mechanism that allows an indirect connection between the handle and the clamp members or jaws. Hence, during the initial stage of the clamping process, there can be a 1:1 ratio between movement of the handle and movement of the clamp members or jaws. However, during the later stage of the clamping process when the clamp members or jaws are sufficiently close to one another, optionally applying sufficient pressure on the atrium, there may not be a 1:1 ratio between movement of the handle and movement of the clamp members or jaws. Rather, a handle movement results in a smaller corresponding movement of the clamp members and jaws. The treatment assemblies can be configured as inserts that are removable with respect to the clamp members or jaws. According to some embodiments, the treatment assemblies may be disposable, replaceable, or both, and the clamp or support member can be sterilizable, reusable, or both.

According to some embodiments, a treatment system can be convertible; that is, the system can convert from a bipolar configuration to monopolar configuration and back to a bipolar configuration according to the surgeon's need or decision. In some cases, a monopolar device does not include jaws and can be in the form of a malleable electrode that presents a contact strip or surface to deliver RF energy to tissue from any direction and from any shape it is bent into. In some cases, a monopolar probe resides within or is a part of the handle or shaft structure of a bipolar clamp. The monopolar electrode can reside in one jaw and act as the active electrode when in a bipolar configuration, and the other jaw can act as the indifferent (ground) electrode. When the surgeon converts the device to a monopolar configuration, for example by pulling the monopolar probe assembly out of the rest of the device, the probe acts as a monopolar device because the return path for energy is now through the ground pad on the patient. When the surgeon is done with the monopolar RF application, he or she may choose to straighten the electrode and reinsert it into the bipolar handle to make that part functional again.

In some embodiments, the treatment system may further include an insulation member at least partially surrounding or covering one or more the actuator assembly, coupling assembly, or clamp assembly. Such an insulation member can operate to protect body structures in the vicinity of the epicardial tissue from being ablated or damaged due to heat or electrical current. In some cases, ablation members such as electrodes 316a, 316b, 317a, 317b may be adjustable to deliver two or more varying amounts of ablative energy to two or more locations on the epicardial tissue. Various embodiments may further include at least one sensor for sensing a quantity of ablation provided by the ablation member to the tissue.

Actuator assembly 320 may include a symmetric, unified release trigger. In some cases, the actuator assembly may have a plurality of separated ratchet teeth. In use, the operator or surgeon may close or clamp the jaw mechanisms together by activating a handle or plunger of the actuator assembly. Relatedly, the operator may release the jaw mechanisms from a clamped configuration by activating a release trigger of the actuator assembly. In some cases, a release trigger may include a button or a slide mechanism. The treatment system may be spring loaded, such that release of a ratchet mechanism allows release of the jaw mechanisms and the spring allows an automatic position return of the ratchet mechanism.

Embodiments of the present invention encompass a variety of mechanisms which may be used to open or close the jaw mechanisms. In some cases, treatment systems may include a pliers assembly configured to open or close the jaw mechanisms. In some cases, treatment systems may include a scissors assembly configured to open or close the jaw mechanisms. Optionally, a pliers or scissors assembly can include two members having a central pivot, whereby the closing of the handle portion closes the distal portions by changing the angle between the two members from something greater than zero to something less than the starting number, generally bringing together the distal ends. In some cases, treatment systems may include a sliding mechanism or assembly configured to open or close the jaw mechanisms. Optionally, the treatment system may include a plunger assembly configured to open or close the jaw mechanisms. Exemplary actuator assemblies may include pistol grips, hinged grips, and the like. In some cases, an actuator assembly may provide for direct activation or coupling of the jaw mechanisms, such that when the surgeon moves a portion of the actuator assembly by a given amount, the actuator assembly causes the jaw mechanism to move the same amount in a 1:1 ratio. In some cases, an actuator assembly may provide for indirect activation or coupling of the jaw mechanisms, such that when the surgeon moves a portion of the actuator by a given amount, the actuator assembly causes the jaw mechanism to move in differing amount. An actuator assembly may be configured to limit, attenuate, or amplify the amount of clamping force applied to a tissue based on the amount of squeezing or activating force manually applied by a surgeon.

In some instances, the treatment system can include a jaw release trigger that is symmetric about two planes, and that allows or actuates release of the jaw mechanisms such that the jaw mechanisms translate relative to each other in an upward or downward manner. Such actuation can be performed without changing the jaw release finger motion. In some cases, a jaw mechanism release or opening action can be accomplished without changing the operator's basic hand position on the handle. The system can be configured so that the operator can reach or use the release trigger located in an ergonomically efficient position. A release trigger may be self-centering and momentary. In some cases, a release trigger can have a single re-centering spring that is captive in the body shell and actuated at either end by a finger that reaches into the entrapping space from the moving trigger portion from either end to compress the spring as the trigger is pushed off-center.

Figure 4:
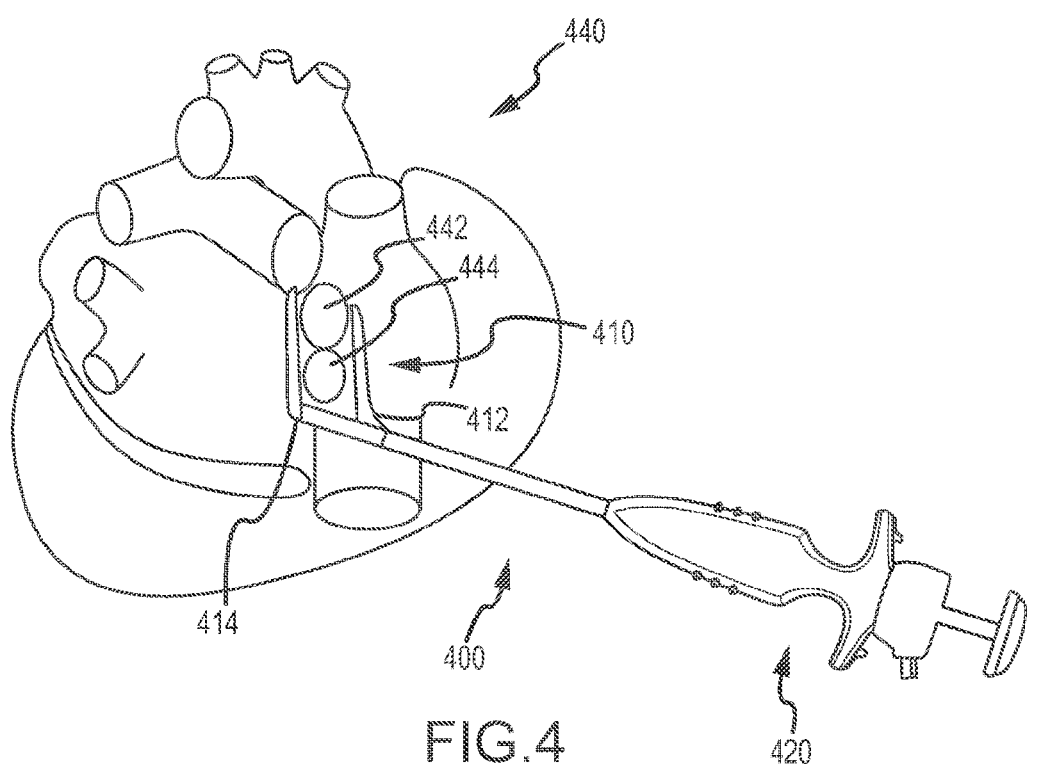
FIG. 4 illustrates aspects of a tissue treatment system according to embodiments of the present invention.

FIG. 4 shows a treatment system 400 in a position for performing an ablation or treatment procedure on epicardial tissue of heart 440. Treatment system 400 includes a clamp assembly 410 having first and second jaw mechanisms 412, 414, and can be configured to ablate in a pattern approximating two lines adjacent the right pulmonary veins 442, 444. As discussed elsewhere herein, jaw mechanisms 412, 414 can be rotated as desired to provide a variety of ablation configurations. Additionally, treatment system 400 may be moved to a variety of positions to ablate multiple patterns in multiple locations on the epicardial tissue.

Treatment system 400 includes a handle or actuator assembly 420 disposed toward a proximal portion of the system. As shown here, first and second jaw mechanisms 412, 414, which may include two bipolar ablation clamps, are disposed toward a distal portion of the system. The jaw mechanisms 412, 414 can be curved or shaped. In some cases, jaw mechanisms 412, 414 are curved and adjustably rotatable, so that for each jaw mechanism 412, 414, a concave portion or arc of the jaw mechanism can face toward the handle, away from the handle, toward the right side of the handle, toward the left side of the handle, or toward any desired direction relative to the handle. In some cases, a jaw mechanism can be in connectivity with a treatment assembly or ESU. During use, the tissue treatment system can be used to contact the cardiac tissue, which can be effectively accomplished for example by the curvature orientation. The curved or contoured shape of the jaw mechanisms can allow the treatment system to be placed on the heart without impinging upon the pulmonary veins. Hence, there is an increased likelihood of ablating tissue of the atrium, as opposed to ablating tissue of the pulmonary veins themselves. Treatment system 400 is well suited for use in surgical methods where access ports are not employed. For example, the treatment system can be inserted into a patient via a 3-4 inch thoracotomy. In use, the jaw mechanisms are placed at or near the ostia, and actuated until the opposing jaw members are approximately 2-5 millimeters apart. This action serves to collapse the atrium near the pulmonary veins. An ablation is performed, and the clamping pressure is released thus allowing the atrium to return to the uncompressed state.

Electrosurgical Unit Operation

Figure 5:
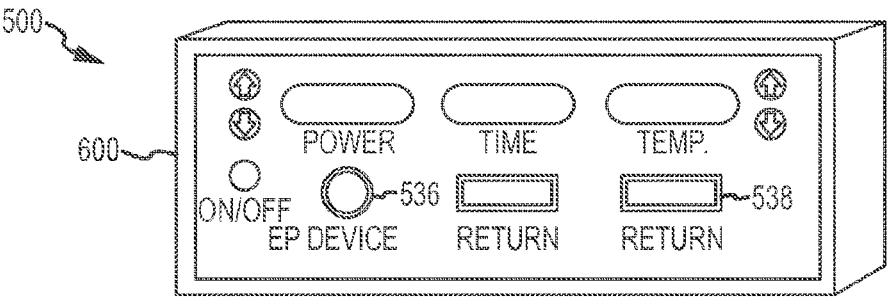
FIG. 5 illustrates aspects of a tissue treatment system according to embodiments of the present invention.
Figure 6A:
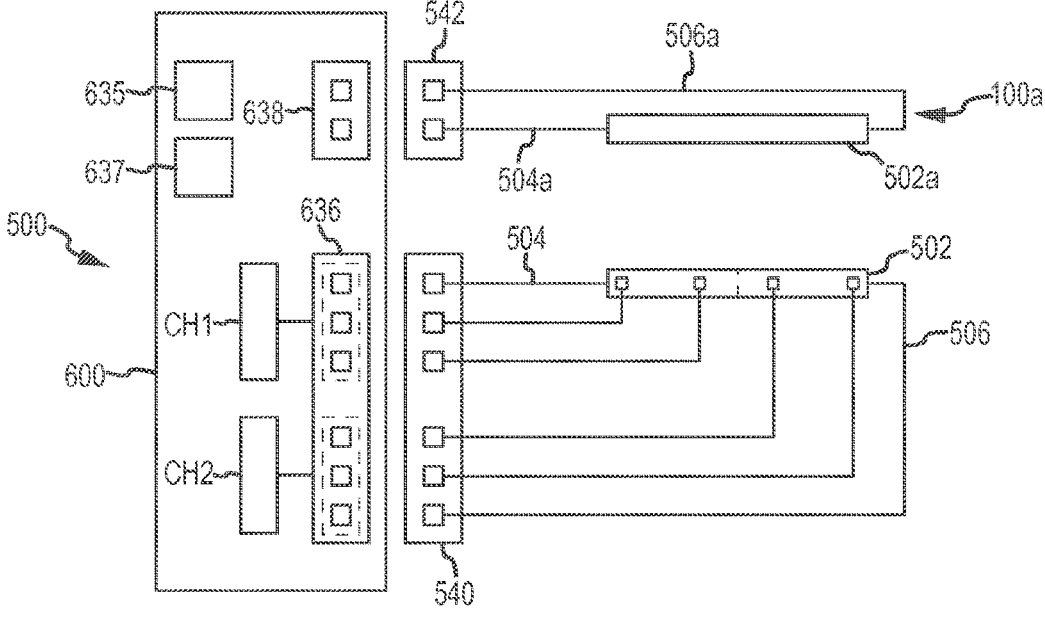
FIGS. 6A and 6B illustrates aspects of a tissue treatment system according to embodiments of the present invention.
Figure 6B:
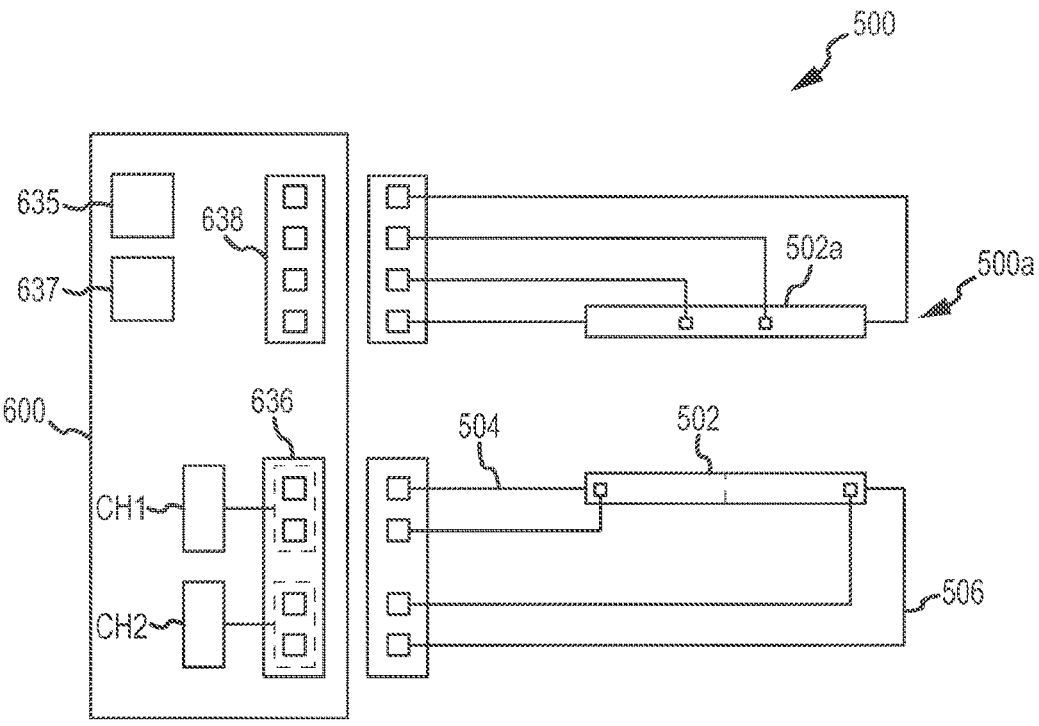

According to some embodiments, a treatment system may include or be coupled in operative association with an electrosurgical unit (ESU) that can supply and control power to an ablation assembly of the treatment system. FIGS. 5, 6A, and 6B illustrate aspects of an ESU 600 that supplies and controls power, such RF power, to a treatment system during a treatment procedure. As shown here, ESU 600 includes a controller 635, a source of RF power 637 that is controlled by the controller, and a plurality of displays and buttons that are used to set the level of power supplied to one or more electrodes at various locations on an electrode. The exemplary ESU 600 illustrated is operable in a bipolar mode, where tissue coagulation energy emitted by an electrode 502 is returned through a return electrode 502a, and a unipolar mode, where the tissue coagulation energy emitted by the electrode is returned through one or more indifferent electrodes (not shown) that are externally attached to the skin of the patient with a patch or one or more electrodes (not shown) that are positioned in the blood pool. The return electrode 502a, which in a bipolar configuration can be identical to the electrode 502, may be connected to the ESU 600 by a pair of power return lines 504a and 506a. The return electrode 502a and power return lines 504a and 506a together define a return electrode assembly 500a.

In some embodiments, return electrode 502a can be an indifferent electrode. In a bipolar configuration, an active electrode and an indifferent electrode can cooperate to help form a complete circuit of RF energy, for example when the two electrodes are placed across an anatomical feature such as the atria or other patient tissue. Energy can travel from the active electrode through the tissue to the indifferent electrode. An active electrode can be coupled with one or more RF wires. An indifferent electrode can provide a return path, optionally as a single wire, operating as a ground. In use, energy passing through the electrodes can raise the temperature of the intervening tissue, for example tissue which is secured between two clamp mechanisms. In turn, the heated tissue can raise the temperature of the electrodes. In some cases, active electrodes, indifferent electrodes, or both, can be cooled with internal cooling mechanisms. In exemplary embodiments, energy applied by the electrodes operates to kill tissue without a significant concomitant rise in tissue temperature. In some instances, a treatment system may include multiple active electrodes along a length of a clamp. Each active electrode can be coupled with an RF wire that supplied energy to the electrode.

ESU 600 can be provided with a power output connector 636 and a pair of return connectors 638. The electrode 502 is connected to the power output connector 636 by way of the power supply lines 504 and 506 and a power connector 540, while the return electrode 502a is connected to one of the return connectors 638 by way of the power return lines 504a and 506a and a return connector 542. In some cases, the ESU output and return connectors 636 and 638 have different shapes to avoid confusion and the power and return connectors 540 and 542 are correspondingly shaped. For example, power connector 540 may have a circular shape corresponding to an ESU power output connector 636 having a circular shape, and return connector 542 may have a rectangular shape corresponding to an ESU return connector 638 having a rectangular shape.

ESU 600 can be configured to individually power and control a plurality of electrodes. In some cases, the electrodes may be about 10 mm in length. Optionally, a bipolar clamp configuration may include two 32 mm active electrodes and one 70 mm electrode. Such individually powered or controlled configurations may be referred to as providing "multi-channel control." In some cases, ESU 600 can include up to 8 channels, or more. ESU 600 can also be configured to individually power and control two or more portions of a single electrode as well as two or more portions of each of a plurality of electrodes during a lesion formation procedure. Electrode 502 as shown here can be divided into two portions for power control purposes. The electrode portion connected to the power supply line 504 on one side of the dash line in FIG. 6A (e.g. the left side) and the electrode portion connected to the power supply line 506 on the other side (e.g. the right side) of the dash line. According to some embodiments, the dash line does not represent a physical division and the electrode 502 is a continuous, unitary structure. Electrode 502 can be placed adjacent to tissue and power to one portion can be controlled by control channel CH1 and power to the other portion is controlled by control channel CH2. The power can be, although not necessarily, supplied to both portions simultaneously.

According to some embodiments, the level of power supplied to the electrode 502 by way of the power supply line 504 may be controlled by the ESU. In one exemplary control scheme, the level of power supplied to the electrode 502 by way of the power supply line 506 can be controlled by the ESU.

The amount of power required to coagulate tissue typically ranges from 5 to 150 w. Aspects of suitable temperature sensors and power control schemes that are based on sensed temperatures are disclosed in U.S. Pat. Nos. 5,456, 682, 5,582,609 and 5,755,715, the contents of which are incorporated herein by reference.

According to some embodiments, a plurality of spaced electrodes can be provided that operate in a unipolar mode. Each of the electrodes can be connected to a respective pair of power supply lines. Each of the electrodes on a surgical probe can be divided into portions for power control purposes, and the level of power supplied to some electrode portions by way of power supply lines can be controlled by the ESU, while the level of power supplied to other electrode portions by way of power supply lines can be controlled by the ESU.

As noted elsewhere herein, in some cases an ESU can be configured to apply voltage pulses of 500-1000 volts between the jaw faces using pulse durations of 0.02-0.1 msec, which in most instances is sufficient to kill all or substantially all myocardial cells between the jaw faces. When it is desired that all or substantially all of the myocardial cells be irreversibly damaged by the high voltage gradients within the targeted tissue, an ESU can be configured to deliver 10-50 pulses over a 1 to 60 second time interval.

Monopolar Ablation Technologies I

For exemplary ablation technologies, including monopolar techniques, that use long linear electrodes, some embodiments use standard return pads on the skin. In such configurations, voltage pulses of 1000-2000 volts applied between the linear electrodes and the return pad with pulse durations of 0.02-0.1 msec can be sufficient to kill all or substantially all myocardial cells within about 5 mm of the electrodes. When it is desired that all or substantially all of the myocardial cells be irreversibly damaged by the high voltage gradients within the targeted tissue, 5-50 pulses can be delivered over a 1 to 60 second time interval. For such electrode configurations and voltage delivery methods, the region of tissue subjected to lethal voltage fields can be determined by the amplitude of the applied pulses and the pulse width. For a 0.05 msec pulse width, multiple 1000 volt pulses are typically sufficient to ablate tissue to a depth of about 5 mm. To achieve reliable lesions depths of about 10 mm, it may be helpful to increase the voltage amplitude to about 2000 volts. In tissue regions that are thick, for example about 10 mm, lesions typically will be also be wide, the lesion having approximately a semicircular cross section. In thinner tissue regions, the lesion width typically will be thinner, being about twice as wide as the tissue is thick. In other words, the lesion will be about 8 mm wide where the atrial wall is about 4 mm thick. Often, there will be little or no cellular damage near the return pads, because with the large surface areas of the pads, the current densities are low at the skin level and therefore voltage gradients are low, generally lower than about 10V/cm.

Figure 7:
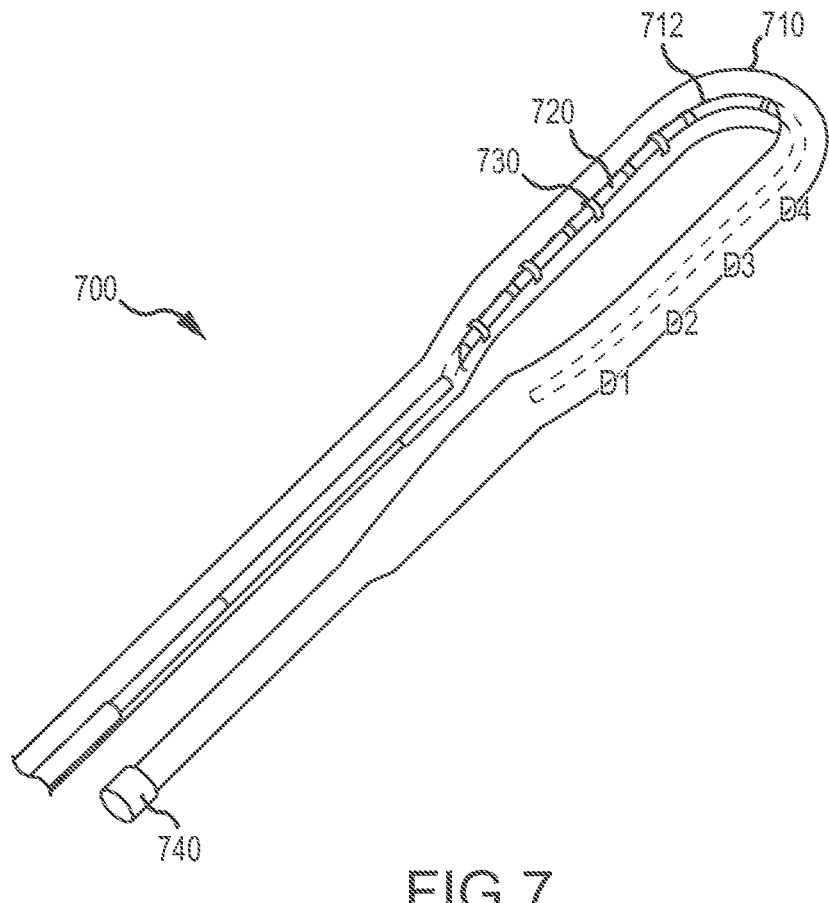
FIG. 7 illustrates aspects of a tissue treatment system according to embodiments of the present invention.

Referring now to the drawings, FIG. 7 illustrates aspects of a tissue treatment system according to embodiments of the present invention. Tissue treatment system 700 is well suited for use in medical procedures that involve ablating cardiac tissue of a human heart, such as those techniques disclosed in U.S. Patent Application Nos. 60/939,201 filed: May 21, 2007, and 61/015,472 filed Dec. 20, 2007. The content of each of these applications is incorporated herein by reference. Tissue treatment system 700 includes a tissue contacting assembly 710, optionally having a suction pod 712. Tissue treatment system 700 also includes a treatment assembly 720 that extends through a length of the tissue contacting assembly. In some cases, tissue treatment system 700 also includes one or more holders 730 that can hold treatment assembly 720 within or relative to tissue contacting assembly 710. Typically, during a surgical procedure the treatment assembly is coupled with an energy source. When a treatment or medical procedure is completed, the treatment assembly may be decoupled from the energy source.

According to some embodiments, a treatment method may include ablating and monitoring a cardiac tissue of a patient with tissue treatment system 700. Treatment methods may also include techniques for placing tissue treatment system 700 at a desired location within a patient. For example, a treatment method may include positioning tissue treatment system 700 at or near the pulmonary veins of a patient. A surgeon or operator may use an obturator and introducer assembly to posit the tissue treatment system at or near a specific location or anatomical feature of the patient. Treatment assembly 720 can include any of a variety of tissue ablation mechanisms. In some cases, a treatment assembly 720 can include an ablation element that transmits or delivers RF energy to patient tissue. Optionally, suitable ablation elements can transmit or deliver infrared laser energy, high intensity focused ultrasound (HIFU) energy, microwave energy, cryoablation energy, and the like. Embodiments encompass treatment assemblies having multiple ablation elements, such as RF electrodes. In some cases, a treatment assembly may include a single ablation element, such as a single RF ablation electrode. Typically, an RF electrode is activated in its entirety during an ablation procedure. Longer lesion lengths can be made by moving the electrode and ablating so that the ablations from the two ablation applications overlap. The procedure can be repeated until the desired lesion pattern is completed.

Figure 8:
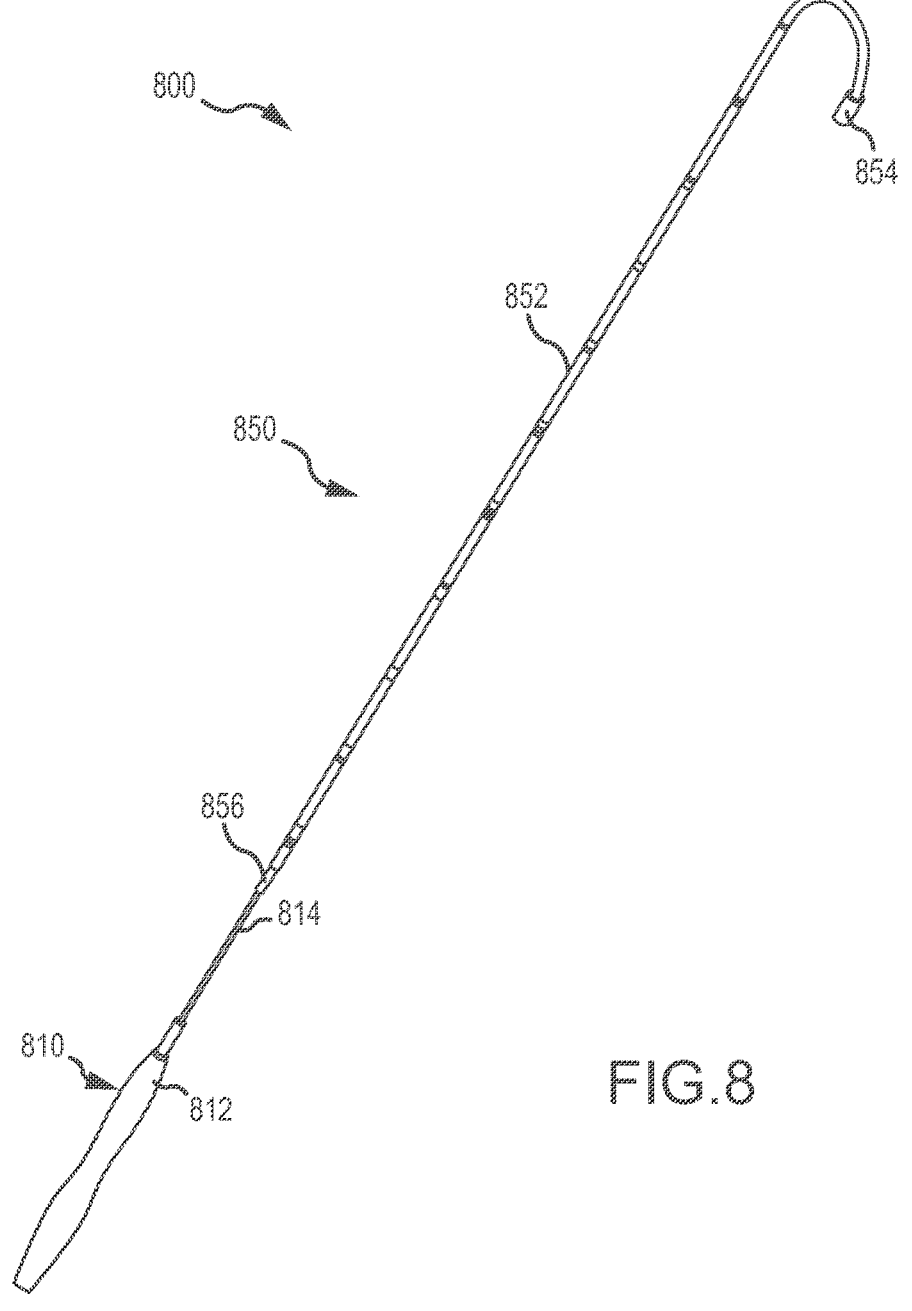
FIG. 8 illustrates aspects of a tissue treatment system according to embodiments of the present invention.

FIG. 8 depicts an obturator and introducer assembly 800 according to embodiments of the present invention. Obturator and introducer assembly 800 includes an obturator 810 and an introducer 850. The introducer includes a tube 852 that is pre-bent or pre-formed into a particular shape, for example a curved or J shape. The obturator includes a handle 812 and a shaft 814. As shown here, obturator shaft 814 can be inserted into introducer tube 852, so that shaft 814 extends substantially through a length of tube 852. The introducer can be fabricated with a relatively flexible material, and the obturator can be fabricated with a relatively rigid material, so that when the obturator is inserted into the introducer, the introducer conforms to or toward the shape of the obturator. When obturator shaft 814 is removed from introducer tube 852, the tube can return to its preformed or pre-bent shape. A distal end 854 of introducer 850 can have a designated region for grasping. During a medical procedure, a grasping instrument may be introduced through the same or a second incision to grasp the distal end or portion 854 of the introducer 850. An operator or surgeon can use the grasping instrument to pull distal end or portion 854 of the introducer outside the body of the patient. A distal end or portion 740 of the tissue treatment system shown in FIG. 7 can be attached with a proximal end or portion 856 of the introducer. Thus, the introducer can be withdrawn or otherwise maneuvered until the tissue treatment system is positioned at or near a desired location within the patient.

According to some embodiments, a treatment method may include inserting an obturator into an introducer, and advancing the combined obturator and introducer assembly through a first incision into the transverse sinus cavity. When the combined assembly has been positioned in a desired area or location at or near the pulmonary veins, the obturator can be withdrawn from the introducer, and the introducer can be allowed to assume a pre-formed shape which may at least partially reach around the pulmonary veins, possibly also guided by contact with the pericardium. In some cases, the introducer is long enough to be inserted from thoracotomy into transverse sinus cavity around the pulmonary veins and out through the oblique sinus and out through the same or a different thoracotomy. Another instrument can be advanced through the same or different thoracotomy to grasp the distal end of the introducer. The introducer can be pulled around the pulmonary veins until the distal end is outside the body of the patient. At this point, both the proximal and distal ends of the introducer can be disposed outside the body of the patient.

A proximal end of introducer can be attached, for example with a luer fitting, to the distal end of a tissue treatment system. The introducer, the tissue treatment system, or both, may include indication markers and lines which an operator can use or rely upon when positioning the tissue treatment system, so as to ensure the desired or proper placement. For example, circumferential indication markers on the introducer can be used as depth measurements, and an indication stripe on the surface of the introducer can be aligned with similar markings on the tissue treatment system to ensure that the ablation device will be facing properly when inserted. In some embodiments, the introducer can have torsional rigidity to facilitate steerability. Further, the introducer can include a material having a highly visible color for endoscopic visualization and distinguishing from natural anatomical colors.

Once the tissue treatment system is in position, suction can be applied to adhere the ablation device to the tissue surrounding the pulmonary veins. The tissue treatment system can be placed into position via any of a variety of suitable techniques, such as those described in U.S. Patent Application Nos. 60/939,201 and 61/015,472 filed May 21, 2007 and Dec. 20, 2007, respectively. The content of each filing is incorporated herein by reference. Ablation energy can be applied. Once treatment is complete, the tissue treatment system can be removed.

According to some embodiments, treatment methods may include performing a medical procedure that entails creating a continuous lesion encircling or partially encircling the pulmonary veins to electrically isolate the pulmonary veins. Treatment methods may also include creating ablation lesions in the left and/or right atrium, vena cava, endocardium to the mitral valve annulus, or along the left atrial appendage to create a Maze-like lesion set for treatment of atrial fibrillation.

Figure 9:
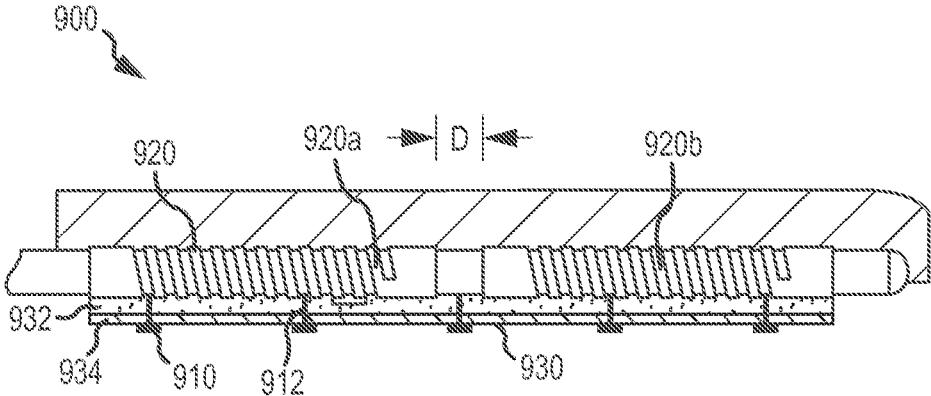
FIG. 9 illustrates aspects of a tissue treatment system according to embodiments of the present invention.

FIG. 9 illustrates aspects of a treatment assembly 900 according to embodiments of the present invention. Such systems can include one or more stimulation electrode for pacing or stimulating tissue. Stimulation electrodes may be used to perform a variety of functions before, during, and after a lesion formation procedure. For example, stimulation electrodes may be used to confirm tissue contact prior to supplying coagulation energy, to evaluate the lesion as the coagulation energy is supplied, and to confirm whether or not a therapeutic lesion has been formed after the coagulation energy has been discontinued. Stimulation energy may be used because non-viable tissue, for example coagulated tissue, is difficult or impossible to stimulate and typically will not propagate stimulation energy to nearby tissue.

Hence, treatment assembly 900 as depicted in FIG. 9 includes one or more pacing or stimulation electrodes 910 that are capable of providing pulses of energy that stimulate, but do not coagulate, tissue. Power delivered to tissue for stimulation purposes will typically be significantly less than that which would form a transmural or otherwise therapeutic lesion in tissue. An exemplary stimulation energy delivery can include two stimulation pulses per second, each pulse being 1 millisecond. In some embodiments, the amplitude can be 10 mA, which would create 5 V, for a total power delivery of 100 μW. In contrast, the amount of power used for coagulating tissue can often range from about 5 to about 150 W. The amplitude may be increased in some instances, for example where the stimulation pulses are being supplied at the same time as the tissue coagulation energy. Treatment assembly 900 also includes one or more ablation or coagulation electrodes 920. The stimulation electrodes can be disposed on energy transmission surfaces of a variable spacing structure 930. Alternatively, the stimulation electrodes may be located between a resilient member 932 and a barrier member 934 or, in instances where there is no barrier member, simply on the exterior of resilient member 932. The stimulation electrodes may also be used in conjunction with a resilient member that includes conductive fibers. A pacing or stimulation electrode 910 may be connected with a signal wire 912. Optionally, a signal wire can be configured such that it will not change the mechanical properties of the resilient material. Suitable signal wires can include wires that are 38 gauge or smaller.

As shown here, signal wire 912 traverses resilient material 932 and can enter a support structure near stimulation electrode 910. For example, a portion of signal wire 912 can be disposed between the windings of an underlying coagulation electrode 920, between two adjacent underlying coagulation electrodes 920, or just proximal to an underlying coagulation electrode 920. A signal line or wire 912 can be configured to provide connectivity between pacing or stimulation electrode 910 and an EP recording apparatus or ESU. One or more stimulation electrodes can be positioned such that they are located between, and aligned with, one or more coagulation electrodes. In some cases, a stimulation electrode can be aligned with a channel, such as a linear channel.

The placement of tissue stimulation electrodes on the same surgical device as the tissue coagulation electrodes allows the physician to quickly and easily confirm tissue contact and evaluate the lesion with little or no movement of the device. Stimulation electrodes can be located between the energy transmitting portions of treatment assembly 900 and can also be located in a current path between treatment assembly 900 and the tissue. This arrangement can provide accurate information when the stimulation electrodes are used to confirm tissue contact prior to supplying coagulation energy, because the stimulation electrodes are in contact with the portions of the tissue structure through which current will be transmitted, as opposed to being in contact with tissue that may be further from the current path.

The location of the stimulation electrodes can also provide accurate information concerning the lesion itself during and after the tissue coagulation procedure because the stimulation electrodes are in direct contact with the coagulated tissue. The assessment of the lesion can be localized. For example, the assessment can be made directly on the target tissue within the current path. Therefore, a lesion assessment process can be easier to implement than those which involve stimulating tissue on one side of a lesion and sensing tissue on the other. Here, the assessment can involve a determination whether or not stimulation of the tissue adjacent to the lesion occurs, as opposed to an assessment of the propagation delay between the stimulation pulse on one side of the lesion and the stimulation on the other.

With respect to methods by which tissue contact may be confirmed after the physician has positioned treatment assembly 900 on a tissue structure, the stimulation electrodes may be used to supply pulses of stimulation energy, sometimes referred to as pacing pulses, to the tissue in the current path CP between treatment assembly 900 and the tissue. The stimulation energy can be supplied through one or more single stimulation electrodes. The physician can monitor the adjacent tissue, either visually or with a monitor such as an ECG to determine whether that tissue was stimulated. In the context of the treatment of atrial fibrillation, for example, the procedure may be performed after treatment assembly 900 is epicardially positioned about one or more of the pulmonary veins. If the stimulation energy stimulates, or paces, the adjacent tissue, for example the left atrium, the physician can know that proper contact has been achieved for the associated portions of treatment assembly 900. This process may be sequentially repeated with any desired combination of stimulation electrodes to insure or evaluate tissue contact with the other portions of treatment assembly 900. Thereafter, and without moving treatment assembly 900, tissue coagulation energy may be applied to the tissue in the current path with one or more coagulation electrodes to form a lesion.

Stimulation energy can be used while the tissue coagulation energy is being supplied in order to determine when a transmural lesion has been completely formed. Here, stimulation energy pulses may be supplied by stimulation electrodes to the tissue in the current path. The tissue adjacent to the current path can be monitored, either visually or with an ECG, to determine when the adjacent tissue is no longer being stimulated. The supply of tissue coagulation energy may be discontinued in response to such a determination. For example, if a tissue treatment system is programmed to supply coagulation energy for 30 seconds, the supply of energy could end after 25 seconds if the lesion is completed earlier than was anticipated, as determined by the inability to stimulate the adjacent tissue. This may be accomplished either manually or automatically.

Tissue may become non-stimulatable before it is irreversibly coagulated or otherwise irreversibly damaged. Accordingly, tissue coagulation energy can continue to be supplied for a few seconds after the adjacent tissue ceases to be stimulated by stimulation energy pulses. That is, there can be a brief delay before the coagulation energy is discontinued. It should also be noted that while coagulation energy is being supplied by the coagulation electrodes, the stimulation energy can be supplied at a significantly higher amplitude, for example 5 times higher, than it would be before or after the coagulation procedure because tissue that is heated can be harder to stimulate. For example, if 4 mA pulses are suitable before and after the coagulation procedure, then 20 mA pulses can be used during the coagulation procedure.

Stimulation energy may be supplied after tissue coagulation energy has been discontinued, either at the end of the pre-programmed period or based on the sensed completion of the lesion, in order to determine whether a transmural lesion has been formed. Without moving treatment assembly 900, stimulation energy pulses may be supplied by stimulation electrodes to the tissue in the current path. The adjacent tissue can be monitored, either visually or with the ECG, to determine whether the adjacent tissue can be stimulated. If not, the physician may assume that a transmural lesion has been formed. In those instances where the lesion is incomplete, one or more stimulation electrodes may be used to determine where the gap, or the portion of the lesion that is not transmural, is located. Additional coagulation energy may then be supplied as necessary or desired to complete the lesion. It may be the case that the entire lesion is not transmural, which may require the coagulation procedure to be at least partially repeated.

Pacing or stimulation electrodes 910 can be relatively small, solid, low profile devices. For example, a stimulation electrode can be configured to be small enough that it does not form transmural myocardial lesions. Suitable surface are sizes can be about 0.2 mm2 to about 10 mm2, and suitable thicknesses can be about 0.01 mm to 0.5 mm. For example, a stimulation electrode can have a surface area of about 1 mm2 and a thickness of about 0.1 mm. Suitable materials include platinum, platinum iridium, stainless steel, gold, silver-silver chloride or other non-toxic metals. Stimulation electrodes may also be formed by coating a conductive material onto variable spacing structures 930 or another underlying structure using conventional coating techniques or an ion beam-assisted deposition (IBAD) process. Suitable conductive materials include platinum-iridium and gold. An undercoating of nickel, silver or titanium may be applied to improve adherence. Conductive ink compounds, such as silver-based flexible adhesive conductive ink (polyurethane binder) or metal-based adhesive conductive inks (e.g. platinum, gold, or copper based) may also be pad printed in place. With respect to assembly, signal wire 912 may be welded or soldered to solid pacing or stimulation electrode 910 prior to assembly, while coated/printed electrodes may be formed onto the ends of signal wires that are already in place.

Exemplary tissue treatment systems and methods can involve providing monopolar stimulation pulses from stimulation electrodes 910. For example, a monopolar stimulation pulse can be generated by a pair of stimulation electrodes 910 which may be associated with one or more coagulation electrodes 920 that form the lesion. Stimulation electrode pairs may be used to supply pulses of stimulation energy to the tissue in the current path CP associated with one of the coagulation electrodes. The physician can monitor the adjacent tissue in the tissue structure, either visually or with an ECG, to determine whether that tissue was stimulated. This process may be sequentially repeated with the other stimulation electrode pairs in order to insure proper tissue contact with the applicable portions of the treatment assembly 900. Thereafter, and without moving treatment assembly 900, tissue coagulation energy may be applied to the tissue in the current path CP with the coagulation electrodes to form a lesion. Stimulation electrodes 910 may also be used to determine lesion depth and, correspondingly, whether or not a lesion is transmural at various points along the length of the lesion. Stimulation energy may be used to determine lesion depth because non-viable tissue, for example coagulated tissue, may not be stimulatable and may not propagate stimulation energy to nearby tissue. As such, when the application of stimulation energy that should stimulate tissue at a known depth fails to do so, and that depth is greater than or equal to the thickness of the body structure, it may be inferred that a transmural lesion has been formed. In some cases, the stimulation electrodes can be used on a coagulation electrode-by-coagulation electrode basis both during and before the coagulation process in the manner described above.

In the context of lesions formed within the heart, for example, localized current densities of at least about 2 mA/cm2 may be needed to stimulate heart tissue. With respect to current transmitted from an electrode to tissue, the current density can be about I/2nr2, where r is the distance from the electrode. Thus, a 1 mA stimulation pulse will typically stimulate viable tissue that is up to about 2.8 mm from the electrode, a 2 mA stimulation pulse will typically stimulate viable tissue that is up to about 4.0 mm from the electrode, a 10 mA stimulation pulse will typically stimulate viable tissue that is up to about 9.0 mm from the electrode, and a 20 mA stimulation pulse will typically stimulate viable tissue that is up to about 13.0 mm from the electrode. The left atrium is, for example, about 3 mm thick and accordingly, failure to stimulate with a 2 mA stimulation pulse indicates that a transmural lesion has been formed in the vicinity of the stimulation electrode. As noted above, these values can be substantially increased, for example by a factor of five, when the stimulation pulses are being supplied at the same time as the coagulation energy.

As shown in FIG. 9, pacing or stimulation electrodes 910 can be positioned between the coagulation electrodes 920 and target tissue. As such, the stimulation electrodes 910 can be in the current path of each coagulation electrode 920. Optionally, stimulation electrodes can be disposed between the current paths associated with coagulation electrodes 920. As described elsewhere herein, treatment assembly 900 can be used in conjunction with a standard return pad placed on the patient's skin. Voltage pulses of 1000-2000 volts, for example generated by an ESU in operative association with treatment assembly 900, can be applied between the linear electrodes and the return pad with pulse durations of 0.02-0.1 msec. Such treatment protocols can be sufficient to kill all or substantially all myocardial cells within about 5 mm of the electrodes. When it is desired that all or substantially all of the myocardial cells be irreversibly damaged by the high voltage gradients within the targeted tissue, 10-50 pulses can be delivered over a 1 to 60 second time interval. For such electrode configurations and voltage delivery methods, the region of tissue subjected to lethal voltage fields can be determined by the amplitude of the applied pulses and the pulse width. For a 0.05 msec pulse width, multiple 1000 volt pulses are typically sufficient to ablate tissue to a depth of about 5 mm. To achieve reliable lesions depths of about 10 mm, it may be useful to increase the voltage amplitude to about 2000 volts.

Figures 10, 11:
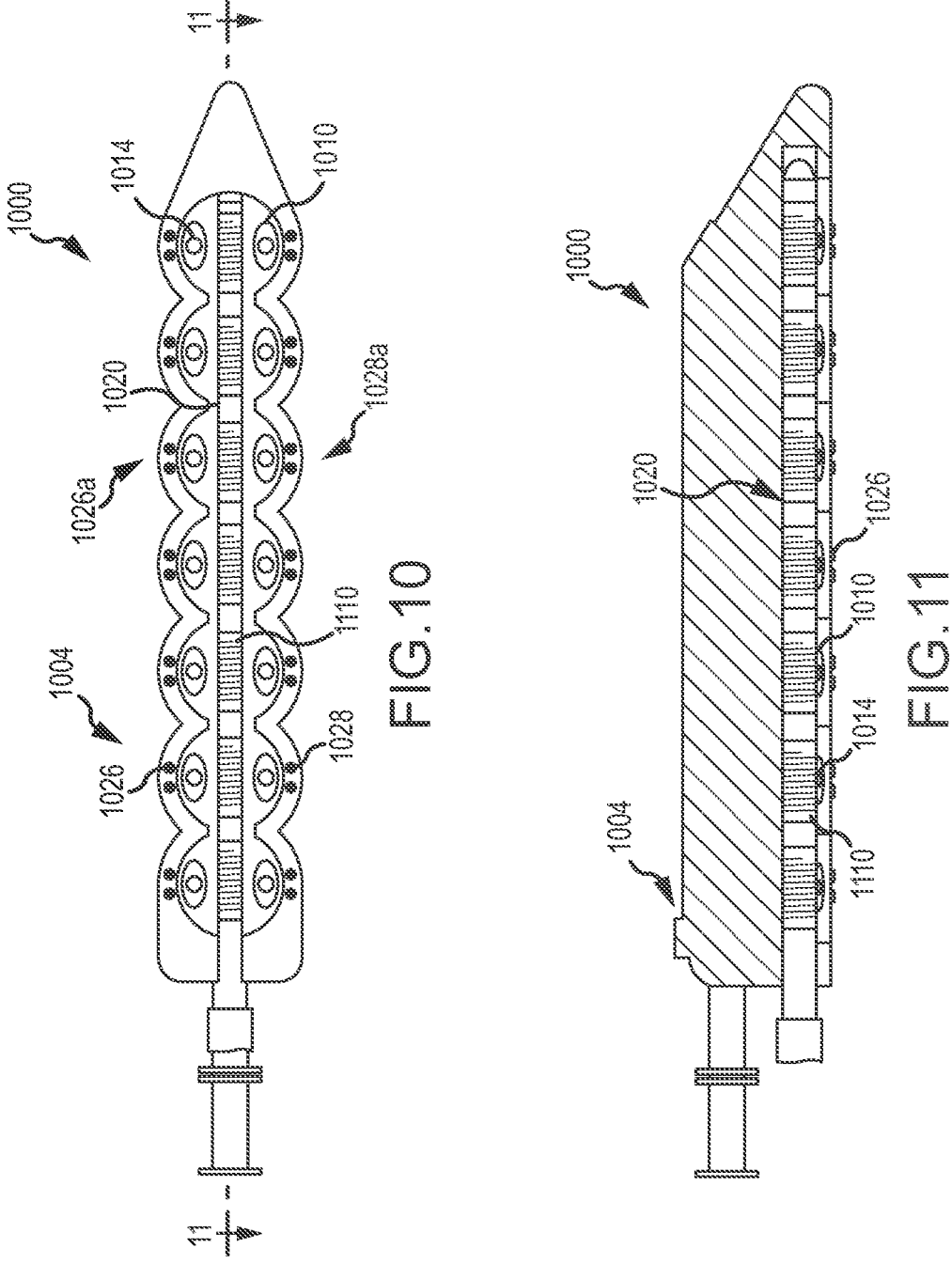
FIG. 10 illustrates aspects of a tissue treatment system according to embodiments of the present invention.
FIG. 11 illustrates aspects of a tissue treatment system according to embodiments of the present invention.

FIGS. 10 and 11 illustrate aspects of a treatment assembly 1000 according to embodiments of the present invention. In addition to forming lesions, treatment assembly 1000 may also be used to determine whether or not therapeutic lesions have been properly formed by, for example, supplying tissue stimulation energy on one side of a lesion. The tissue on the other side of the lesion may then be monitored to determine whether an excitation block, typically the result of a continuous transmural lesion, has been formed in the target tissue. Tissue stimulation energy may also be used to determine lesion depth, which in turn, allows the physician to determine whether or not a lesion is transmural. In the exemplary implementations, the tissue stimulation energy is provided by treatment assembly 1000 that is capable of providing a pulse of energy that stimulates, but does not coagulate, tissue. An exemplary treatment assembly 1000 may be coupled with a conventional pacing apparatus, such as an external pulse generator. An ECG machine that is capable of monitoring and recording electrical impulses sensed by electrodes may also be in connectivity with treatment assembly 1000.

As described elsewhere herein, treatment assembly 1000 can be used in conjunction with a standard return pad placed on the patient's skin. Voltage pulses of 1000-2000 volts, for example generated by an ESU in operative association with treatment assembly 1000, can be applied between the linear electrodes and the return pad with pulse durations of 0.02-0.1 msec. Such treatment protocols can be sufficient to kill all or substantially all myocardial cells within about 5 mm of the electrodes. When it is desired that all or substantially all of the myocardial cells be irreversibly damaged by the high voltage gradients within the targeted tissue, 10-50 pulses can be delivered over a 1 to 60 second time interval. For such electrode configurations and voltage delivery methods, the region of tissue subjected to lethal voltage fields can be determined by the amplitude of the applied pulses and the pulse width. For a 0.05 msec pulse width, multiple 1000 volt pulses are typically sufficient to ablate tissue to a depth of about 5 mm. To achieve reliable lesions depths of about 10 mm, it may be useful to increase the voltage amplitude to about 2000 volts.

With respect to the stimulation energy, the power delivered to tissue for stimulation purposes will typically be significantly less than that which would form a transmural or otherwise therapeutic lesion in tissue. Stimulation electrodes may also be used for sensing. An exemplary stimulation energy delivery can include two stimulation pulses per second, each pulse being 1 millisecond long or wide. In some cases, a maximum amplitude can be 20 mA, which can create 10 V, for a total power delivery of 400 µW. Another exemplary stimulation energy delivery can include of two stimulation pulses per second, each pulse being 1 millisecond long or wide. In some cases, a maximum amplitude can be 10 mA, which can create 5 V, for a total power delivery of 100 µW. The amount of power required to coagulate tissue may in some instances range from 5 to about 150 W.

Treatment assembly 1000 can be in connectivity with a pacing apparatus or an EP recording apparatus via any suitable mechanisms. In some cases, a tissue treatment system can be configured so that coagulation electrodes will only receive coagulation energy and stimulation electrodes will only receive stimulation energy. The functionality of a tissue stimulation apparatus and EP recording apparatus may be combined into a single device. An EP recording apparatus may be configured to display measured conduction delays. Optionally, an EP recording apparatus may be used to store expected propagation delays for various tissue types and suction device configurations, including the positioning of the stimulation and sensing electrodes. An EP recording apparatus can compare the expected propagation delay (e.g. 10 ms) with no block to the measured propagation delay (e.g. 50 ms) and determine whether or not a complete conduction block has been formed. An EP recording apparatus can then provide an audible or visual indication concerning the status of the lesion. Alternatively, conduction block can be determined by comparing a pre-treatment conduction delay, for example 20 ms, to a conduction delay during or following ablation. An increased conduction delay of more than a predetermined value for example 30 ms indicates a successful ablation attempt at the site. In the above example a conduction delay of 50 ms or more would indicate ablation success.

Embodiments of the present invention may be used to test the effectiveness of a lesion in any of a variety of ways. For example, after the lesion is formed, the physician may use the same surgical device that was used to form the lesion, such as a tissue treatment system that includes treatment assembly 1000, to perform a lesion evaluation. Stimulation electrodes that are provided on treatment assembly 1000 may be used to stimulate tissue on one side of a lesion by pacing at a higher rate than normal, for example 120 beats/minute. The local activation, if any, on the other side of the lesion can indicate whether or not the excitation block is incomplete. The stimulation electrodes may also be used to sense tissue within an isolated tissue region around which a lesion has been formed. Local activation within the isolated region from the heart's natural stimulation is indicative of a gap in the lesion. Additionally, the stimulation electrodes may be used to determine lesion depth. The placement of tissue stimulation electrodes on the same surgical device as the tissue coagulation electrodes can allow the physician to quickly and easily evaluate a lesion after it has been formed.

Treatment assembly 1000 can include a suction device 1004, longitudinally extending bipolar pairs of tissue stimulation electrodes 1026, and longitudinally extending bipolar pairs of sensing electrodes 1028 near the lateral edges of the suction device. A plurality of bipolar pairs of stimulation electrodes 1026 can extend along a length of one side of the suction device 1004, and a plurality of bipolar pairs of sensing electrodes 1028 can extend along a length of the other side of the suction device. Each bipolar pair can be adjacent to one of the suction ports 1010, 1014 and, accordingly, the electrodes can be held firmly against tissue when suction force is applied. Stimulation electrodes 1026 can be located on one side of a slot 1020 and sensing electrodes 1028 can be located on the other side. As such, the tissue stimulation and sensing electrodes 1026 and 1028 can be on opposite sides of treatment assembly 1000, on opposite sides of coagulation electrodes 1110, and on opposite sides of a lesion formed by the coagulation electrodes.

Embodiments of the present invention encompass a wide variety of alternative stimulation and sensing electrode schemes. By way of example, but not limitation, the number of bipolar pairs of tissue stimulation and sensing electrodes 1026 and 1028 may range from a large number of pairs, as shown, to a single pair tissue stimulation electrodes and a single pair sensing electrodes. The single pairs may be located near the middle, measured longitudinally, of suction device 1004. Another alternative is unipolar stimulation and sensing. Here, single stimulation electrodes, as opposed to a bipolar pair, may be positioned adjacent to each of the suction ports 1010 on one side of the suction device 1004 and single sensing electrodes may be positioned adjacent to each of the suction ports on the other side of the suction device.

With respect to configuration and manufacture, the exemplary tissue stimulation and sensing electrodes 1026 and 1028 may be relatively small, low profile devices. For example, the electrodes may be too small to form transmural myocardial lesions. Suitable sizes may be about 0.5 mm to 1 mm in diameter, and a suitable thickness may be about 0.01 mm. Such electrodes may be formed by coating a conductive material onto the suction device 1004 using conventional coating techniques or an IBAD process. Suitable conductive materials include platinum-iridium and gold. An undercoating of nickel, silver or titanium may be applied to improve adherence. Conductive ink compounds, such as silver-based flexible adhesive conductive ink (polyurethane binder) or metal-based adhesive conductive inks (e.g. platinum, gold, or copper based) may also be pad printed onto the suction device 1004. A stimulation electrode can be connected with a signal wire or line. In some cases, a signal lines may be very thin (e.g. about 40-50 gauge wire).

An exemplary tissue treatment system may be used to test the quality of lesions formed during a lesion formation procedure in a variety of ways. For example, a suction source may be used to maintain the position of the suction device 1004 after power transmission from the coagulation electrodes 1110 has ended. A pulse of stimulation energy, for example about 10 mA, may be applied to viable tissue on one side of the lesion by a pair of stimulation electrodes 1026*a*. The viable tissue on the other side of the lesion may be monitored with a pair of sensing electrodes 1028*a* to detect the local excitation from the pulse of stimulation energy. Treatment assembly 1000 can be used to measure the amount of time between the delivery of the pulse to the tissue by the stimulation electrode pair 1026*a* and the detection of the local activation by the sensing electrode pair 1028*a* on the other side of the lesion. The conduction delay, or amount of time that between pulse delivery on one side of the lesion and local activation on the other can be indicative of the quality or extent of the lesion.

In the context of the formation of lesions within the heart, the conduction delay from the stimulation electrode pair 1026*a* and the sensing electrode pair 1028*a* will typically be about 10 ms when the distance between the pairs is about 1 cm, absent a conduction block. Here, the excitation pulse may travel a relatively short distance. Conversely, when a complete conduction block is formed between the stimulation and sensing pairs, the excitation pulse may be forced to travel around the lesion. The longer travel distance can result in a longer conduction delay, which is indicative of the formation of a therapeutic lesion. For example, a continuous 50 cm transmural lesion that creates a complete conduction block along its length will typically increase the conduction delay to about 50 ms.

In some embodiments, a lesion can be tested at various points along its length, one point at a time. The lesion may be tested with each of the stimulation and sensing electrode pairs that are adjacent to a coagulation electrode that was used to form a lesion. If for example, the proximal four coagulation electrodes are used to form a lesion, then the proximal four pairs of stimulation and sensing electrodes will be used, one stimulation/sensing at a time, to determine whether or not the lesion creating procedure created a complete conduction block. In some cases, if a pacing pulse is able to cross the lesion, the heart will beat faster, for example 120 beats/minute. This may be determined by observation or by use of an ECG machine that is monitoring the heart. Additional coagulation may be used to complete an incomplete lesion. Because muscle bundles are not always connected near the pulmonary veins, it may be desirable to apply stimulation energy to a number of tissue areas to reduce the possibility of false negatives. Stimulation electrodes may be used to monitor tissue within a region that was intended to be isolated. In the context of pulmonary vein isolation, for example, stimulation electrodes may be placed in contact with viable tissue on the pulmonary vein side of the lesion. Local activation within the isolated region from the heart's natural stimulation is indicative of a gap in the lesion. Treatment assembly 1000 may be used to determine whether or not a lesion is transmural. Tissue stimulation electrodes may be connected to a tissue stimulation apparatus and used to provide stimulation energy. Tissue stimulation electrodes may also be used for sensing local tissue activation. Stimulation electrodes may operate in a bipolar mode, and also may operate in unipolar mode.

In some tissue treatment system or method embodiments, coagulation electrodes can be configured to transmit RF energy. Optionally, other types of coagulation elements, such as such as lumens for chemical ablation, laser arrays, ultrasonic transducers, microwave electrodes, ohmically heated hot wires, and the like may be substituted for or supplement the coagulation electrodes. Coagulation electrodes may be arranged as a series of spaced electrodes. Optionally, a single elongate coagulation electrode may be employed. Coagulation electrodes can be in the form of wound, spiral closed coils. The coils can be made of electrically conducting material, such as copper alloy, platinum, or stainless steel, or compositions such as drawn-filled tubing, for example a copper core with a platinum jacket. The electrically conducting material of the coils can be further coated with platinum-iridium or gold to improve its conduction properties and biocompatibility.

In the case of laser ablation, some versions include an end firing diode that can be automatically moved so as to direct energy toward several distinct locations along a line or path. In some versions, a laser beam is transmitted down a control diffracting mechanism, and reflected along a direction orthogonal to the longitudinal axis of the device. Hence, light can be dispersed in a uniform fashion along the diffracting mechanism. Laser ablation techniques according to embodiment of the present invention can involved these types of laser approaches, as well as related techniques which are described in U.S. Pat. Nos. 6,071,302 and 6,270,492, the contents of which are incorporated herein by reference.

Optionally, coagulation electrodes 1110 may be in the form of solid rings of conductive material, like platinum-iridium or gold, coated upon the device using conventional coating techniques or an ion beam assisted deposition (IBAD) process. For better adherence, an undercoating of nickel, silver or titanium can be applied. The coagulation electrodes can also be in the form of helical ribbons. The electrodes can also be formed with a conductive ink compound that is pad printed onto a non-conductive tubular body. A conductive ink compound can include a silver-based flexible adhesive conductive ink (polyurethane binder), however other metal-based adhesive conductive inks such as platinum-based, gold-based, copper-based, etc., may also be used to form electrodes. Such inks may be more flexible than epoxy-based inks. Open coil electrodes may also be employed for coagulation.

Exemplary flexible coagulation electrodes 1110 can be about 4 mm to about 20 mm in length. In some embodiments, the electrodes are about 12.5 mm in length with about 1 mm to about 3 mm spacing, which can result in the creation of continuous lesion patterns in tissue when coagulation energy is applied simultaneously from adjacent electrodes through tissue to an indifferent electrode. For rigid coagulation electrodes, the length of each electrode can vary from about 2 mm to about 10 mm. The diameter, whether flexible or rigid, will typically be about 3 mm. For cardiovascular applications, the length will sometimes range from between about 2 cm and 8 cm in those instances where power is supplied at both longitudinal ends of each electrode, and the end to end resistance is about 5 ohm to about 15 ohm. The diameter of the electrodes may in some cases range from about 1.5 mm to about 3 mm for cardiovascular applications and, in some embodiments, the outer diameter is about 2 mm.

A tissue treatment system may include one or more temperature sensors which can help provide temperature readings and facilitate improved temperature control. As such, the actual tissue temperature can correspond to the temperature set by the physician on the power supply and control device, thereby providing the physician with control of the lesion creation process and reducing the likelihood that embolic materials will be formed. A reference thermocouple may also be provided.

A power supply and control system can include an electrosurgical unit (ESU) that supplies and controls RF power. An ESU can be is capable of supplying and controlling power on an electrode-by-electrode basis, in a "multi-channel control." An ESU can transmit energy to the coagulation electrodes and receives signal from the temperature sensors via any suitable connectivity. An ESU can be operable in a bipolar mode, where tissue coagulation energy emitted by one of the coagulation electrodes is returned through one of the other coagulation electrodes, and a unipolar mode, where the tissue coagulation energy emitted by the coagulation electrodes is returned through one or more indifferent electrodes that are externally attached to the skin of the patient with a patch, or one or more electrodes that are positioned in the blood pool, and a cable. It is also possible to supply power in a combined bipolar/unipolar mode. An ESU can individually power and control each coagulation electrode 1110, optionally based on the hottest of the two measured temperatures at that particular electrode.

Embodiments of the present invention encompass tissue treatment systems and methods for verifying electrical conduction block across ablation lesions and for verifying the effectiveness of an ablation procedure in creating an electrical conduction block across the cardiac tissue. An exemplary verification system includes a conduction block-verification mechanism such as a pacing probe or electrode. A verification method can involve transmitting an electrical pulse to a patient tissue so as to stimulate the tissue. In some cases, the electrical pulse is applied at a rate higher than the intrinsic atrial or ventricular contraction rate or heart rate. A measurement of the pacing threshold, or the minimum voltage or amperage required to excite the tissue, above the intrinsic excitation rate, can be recorded or monitored prior to, during, and following completion of one or more ablation lesions, which may be aimed to isolate specific regions of the heart.

In use, a tissue treatment system can be used to directly contact the epicardium of the heart and transmits electrical energy to electrically stimulate the heart. Such electrical energy can be delivered by a pulse generator that is coupled with or integral to the tissue treatment system. In some cases, an operator can position the tissue treatment system using direct or endoscopic visualization of the tissue surface. Optionally, an operator can monitor, verify, or evaluate a conduction block with the assistance of an ECG recorders. A tissue treatment system can be configured to transmit electrical pacing pulses of variable amplitude up to 20 mA or 10 V in amplitude to pace the heart above normal sinus rhythm, optionally up to 200 BPM to the target anatomical area of the epicardium. A tissue treatment system may also be capable of passively transmitting electrical pulses from the heart to an ECG recorder.

A tissue treatment method may include the temporary pacing of a portion of the heart, for example the left atrium, and the verification or evaluation of an electrical conduction block across one or more ablation lesions. Such methods can provide an indication of lesion continuity and electrical isolation of one or more specific regions on the heart. A tissue treatment system can be used after creating a set of lesions on the epicardium of the left atrium encircling the pulmonary veins in conjunction with surgical, interventional cardiology, or electrophysiology treatments for atrial fibrillation to determine if or to what extent electrical conduction block is achieved.

A tissue treatment system can be used to pace the left atrium by contacting the left atrium both inside and outside an encircling lesion around the pulmonary veins. If significantly more voltage or current is required to pace the heart from inside the encircling lesion as opposed to outside, an inference of electrical isolation of the pulmonary veins can be made. Exemplary methods can be used to assess electrical isolation of several regions of the heart across ablation lesions during surgical treatment of atrial fibrillation, open or minimally invasively, epicardially or endocardially. A pulse generator can supply a higher than normal pacing rate and electrical impulse at variable amplitudes. The tissue treatment system can be used to contact the left atrium within the encircling lesion adjacent to the pulmonary veins and paced to determine if electrical isolation or block was successful. If block is not successful, then the impulse may be captured outside the encircling lesion and pacing of the entire heart may take place.

Embodiments of the present invention encompass tissue treatment systems and methods that provide for the selective activation and deactivation of one or more stimulation or pacing electrodes, optionally based on an evaluation of the conduction block status of a patient tissue. Embodiments also encompass methods that involve determining or identifying a set of one or more stimulation or pacing electrodes for activation. Relatedly, embodiments also encompass methods that involve determining or identifying a set of one or more coagulation electrodes for activation. In some cases, tissue treatment systems can be configured to activate one or more stimulation electrodes or coagulation electrodes based on a determination of whether a treatment assembly of the tissue treatment system is in appropriate contact with the patient tissue. Relatedly, tissue treatment systems can be configured to modulate the amount of energy transmitted by one or more stimulation electrodes or coagulation electrodes based on a determination of whether a treatment assembly of the tissue treatment system is in appropriate contact with the patient tissue. In some cases, tissue treatment systems can be configured to activate one or more stimulation electrodes or coagulation electrodes based on a determination or evaluation of the conduction block status of a patient tissue. For example, a method may involve activating a coagulation electrode which is disposed at or near tissue not having a conduction block, and deactivating or not activating a coagulation electrode which is disposed at or near tissue that has a conduction block. Optionally, tissue treatment systems can be configured to modulate the amount of energy transmitted by one or more stimulation electrodes or coagulation electrodes based on a determination or evaluation of the conduction block status of a patient tissue. Relatedly, a tissue treatment system can be configured to activate or deactivate one or more stimulation electrodes or coagulation electrodes based on a determination or evaluation of whether a treatment assembly of the tissue treatment system is in appropriate contact with the patient tissue and a determination or evaluation of the conduction block status of a patient tissue. A tissue treatment system can also be configured to modulate the amount of energy transmitted by one or more stimulation electrodes or coagulation electrodes based on a determination or evaluation of whether a treatment assembly of the tissue treatment system is in appropriate contact with the patient tissue and a determination or evaluation of the conduction block status of a patient tissue.

According to some embodiments, tissue treatment system can be configured to perform a conduction block test or evaluation during a coagulation or RF procedure, and to modulate the amount of coagulation or ablation energy that is applied by the system to the patient's tissue. For example, a tissue treatment system can be configured to determine when or where to initiate, increase, stop, or reduce power to one or more coagulation electrodes of a treatment assembly based on a conduction block analysis. Similarly, a tissue treatment system can be configured to control when or where and in what amount energy is applied via one or more coagulation electrodes of a treatment assembly based on a conduction block analysis. Often, such methods can involve determining when to stop at least a portion of an ablation treatment. Relatedly, methods can involve stimulating a patient tissue to determine where a conduction block has been established, or at least partially established.

In some embodiments, a tissue treatment system can include or be in connectivity with a coagulation energy generator, such as an RF energy generator, which may include an integrated control mechanism for modulating the output of the generator based on the conduction block status of a patient tissue. In some cases, a tissue treatment system includes a treatment assembly that is configured to apply a pacing or stimulation energy to the tissue via one or more coagulation electrodes. Standard ablation or coagulation electrodes are typically larger than standard stimulation electrodes, because ablation electrodes usually deliver greater amounts of current. Hence, stimulation of tissue with an ablation electrode involves the application of more current than would otherwise be applied with a stimulation electrode. Generally, stimulation of tissue is initiated by a particular current density in the tissue. Due to current dissipation in the tissue, as the surface area of an electrode is increased there is a corresponding proportional increase in the current to the electrode for stimulation. If there is a ten fold increase in the electrode surface area, a ten fold increase in the current amplitude is needed to achieve the current density required for tissue stimulation (the voltage remains substantially unchanged). In many cases, the application of about 2 to 10 volts through an electrode is sufficient to stimulate a tissue independent of electrode size, but the required current is greater for larger electrodes.

In some embodiments, a coagulation electrode that is used to deliver stimulation energy can be configured to output 100 to 200 milliamps, while maintaining a compliance of 10 to 20 volts. In some cases, an RF electrode can be configured to deliver energy at 460 kHz, which may require a pacing circuit having a blocked return path. A two stage LC circuit can be used for passive stimulation. Relatedly, a tissue treatment system can have a first circuit for pacing and a second circuit for ablation, where the first and second circuits are isolated from one another. In some cases, an LC circuit can be configured with a low impedance path at low frequencies used for pacing and a high impedance at ablation frequencies.

Embodiments of the present invention also encompass a tissue treatment system having an integrated ESU with a user interface that provides output signifying the status of one or more lesions. For example, a user interface can identify or show where ablation is successful or where there is a gap in a linear lesion. Relatedly, a user interface can show electrodes or otherwise provide a representation of one or more electrodes and their positioning at or near patient tissue. In some cases, a user interface can reconstruct a model of the heart to identify areas of successful and unsuccessful ablation. Where a touch screen is used, the operator can touch the screen to identify where additional ablation attempts should be done.

An exemplary treatment method can include applying a first ablative energy to a first tissue location via a first electrode, and applying a second ablative energy to a second tissue location via a second electrode. The method can also include performing a detection or monitoring step before, during, or after applying the first and second ablative energies. The method can include detecting a subthreshold electrical conductivity for the first tissue location and a threshold electrical conductivity for the second tissue location, and discontinuing or diminishing application of the first ablative energy to the first tissue location while continuing application of the second ablative energy to the second tissue location. In a related embodiment, an exemplary treatment method includes activating one or more coagulation electrodes of a treatment assembly, applying energy to a patient tissue with the activated coagulation electrodes, performing a conduction block or lesion pattern analysis of the patient tissue, and adjusting the activation level of one or more of the coagulation electrodes based on the conduction block or lesion pattern analysis.

Embodiments also encompass selective deactivation methods using a tissue treatment system. For example, a tissue treatment method can involve activating one or more coagulation electrodes of a treatment assembly, continuing application of a first ablative energy to a first tissue location via a first ablation electrode, and discontinuing or reducing application of a second ablative energy to a second tissue location via a second ablation electrode after detecting a conduction block at or near the second tissue location. Similar embodiments involve operating a treatment assembly during a cardiac surgical procedure, evaluating a conduction block condition at a first tissue location, and discontinuing application of a first ablative energy to the first tissue location in response to the condition of the conduction block at the first tissue location, and continuing application of the second ablative energy to the second tissue location, optionally in response to a conduction block status of the second tissue location. Further, exemplary methods can involve operating an ablation assembly during a cardiac surgical procedure, evaluating a conduction block condition of a patient tissue treatment site, and based on the evaluation of the conduction block condition, continuing application of a first ablative energy to a first tissue location, and discontinuing or reducing application of a second ablative energy to a second tissue location.

Monopolar Ablation Technologies II

For monopolar ablation technologies with long linear electrodes, some embodiments involve using pairs of electrodes spaced more than about 2 cm apart to apply the ablating voltage pulses. For example, with reference to FIG. 9, electrodes 920a and 920b can be separated by a distance D, and distance D may be more than about 2 cm. In such configurations, voltage pulses of 1500-3000 volts applied between the spaced-apart electrodes with pulse durations of 0.02-0.1 msec can be sufficient to kill all or substantially all myocardial cells within about 5 mm of each of the electrodes. When it is desired that all or substantially all of the myocardial cells be irreversibly damaged by the high voltage gradients within the targeted tissue, 10-50 pulses can be delivered over a 1 to 60 second time interval. For such electrode configurations and voltage delivery methods, the region of tissue subjected to lethal voltage fields can be determined by the amplitude of the applied pulses and the pulse width. For a 0.05 msec pulse width, multiple 1500 Volt pulses can be sufficient to ablate tissue to a depth of about 5 mm at each electrode. To achieve reliable lesions depths of about 10 mm, it may be useful to increase the voltage amplitude to about 3000 volts. In tissue regions that are thick, for example about 10 mm, lesions typically will be also be wide, the lesion having approximately a semicircular cross section. In thinner tissue regions, the lesion width typically will be thinner, being about twice as wide as the tissue is thick. In other words, the lesion will be about 8 mm wide where the atrial wall is about 4 mm thick.

Monopolar Ablation Technologies III

For monopolar ablation technologies with long linear electrodes, other embodiments use one polarity for one electrode (A), and an opposite polarity is applied to multiple similar sized electrodes (B), each spaced more than about 2 cm apart from electrode (A) to apply the ablating voltage pulses. For example, (A) and (B) electrodes can be linearly arranged as follows:

BBBBBABBBB where the distance between the (A) electrode and each of the two (B) electrodes adjacent to the (A) electrode is greater than 2 cm. In such configurations, voltage pulses of 1000-2000 volts 30 applied between the spaced-apart electrodes with pulse durations of 0.02-0.1 msec typically are sufficient to kill all or substantially all myocardial cells within about 5 mm of electrode (A). When it is desired that all or substantially all of the myocardial cells be irreversibly damaged by the high voltage gradients within the targeted tissue, 5-50 pulses can be delivered over a 1 to 60 second time interval. For such electrode configurations and voltage delivery methods, the region of tissue subjected to lethal voltage fields can be determined by the amplitude of the applied pulses and the pulse width. For a 0.05 msec pulse width, multiple 1000 Volt pulses typically are sufficient to ablate tissue to a depth of about 5 mm at electrode (A). To achieve reliable lesions depths of about 10 mm at the electrode (A) location, it may be useful to increase the voltage amplitude to about 2000 volts. In tissue regions that are thick, for example about 10 mm, lesions typically will be also be wide, the lesion having approximately a semicircular cross section. In thinner tissue regions, the lesion width typically will be thinner, being about twice as wide as the tissue is thick. In other words, the lesion will be about 8 mm wide where the atrial wall is about 4 mm thick. Lesion depths at electrodes (B) locations usually will be less than those produced at electrode (A) locations. In some instances, the lesion depths at electrode (B) locations will be lower than at electrode (A) locations, when three or more electrodes (B) are used. In some cases, this ablation mode can be carried out without the use of a surface return electrode, while retaining the lower voltage pulse amplitudes involved with ablating tissue.

Other Ablation Technologies

For ablation technologies with long linear electrodes, some embodiments use pairs of electrodes spaced about 4 mm to about 10 mm apart to apply the ablating voltage pulses. In exemplary embodiments, electrodes can be separated by a distance similar to the tissue wall thickness. In such cases, more than two electrodes can be so connected. FIG. 12 shows aspects of an ablation system 1200 according to embodiments of the present invention. Ablation system 1200 can include multiple electrodes 1210 linearly mounted on a catheter shaft 1220. For example, system 1200 can include ten electrodes linearly mounted on catheter shaft 1220. In some instances, the odd numbered electrodes (e.g. 1, 3, 5, 7, and 9) can be connected to one voltage polarity and the even numbered electrodes (e.g. 2, 4, 6, 8, and 10) can be connected to an opposite voltage polarity. An atrial wall thickness is generally about 4 mm or more in patients with atrial fibrillation. Hence, an exemplary edge-to-edge separation distance D between electrodes can be about 6 mm. In some cases, an electrode length L can be 1-2 times as long as the distance between electrodes. In such a configuration, voltage pulses of 1500-3000 volts applied between the spaced-apart electrodes with pulse durations of 0.02-0.1 msec typically are sufficient to kill all or substantially all myocardial cells within about 5 mm of each of the electrodes. When it is desired that all or substantially all of the myocardial cells be irreversibly damaged by the high voltage gradients within the targeted tissue, 5-50 pulses can be delivered over a 1 to 60 second time interval. For such electrode configurations and voltage delivery methods, the region of tissue subjected to lethal voltage fields can be determined by the amplitude of the applied pulses and the pulse width. For a 0.05 msec pulse width, multiple 1500 volt pulses typically are sufficient to ablate tissue to a depth of about 5 mm at each electrode. To achieve reliable lesions depths of about 10 mm, it may be useful to increase the voltage amplitude to about 3000 volts. In tissue regions that are thick, for example about 10 mm, lesions typically will be also be wide, the lesion having approximately a semicircular cross section. In thinner tissue regions, the lesion width typically will be thinner, being about twice as wide as the tissue is thick. In other words, the lesion will be about 8 mm wide where the atrial wall is about 4 mm thick. Electrode configurations such as those depicted in FIG. 12 are well suited for use with the tissue treatment system shown in FIG. 7, as well as various suction-based lesion forming minimally invasive ablation probes.

Effects of Voltage Pulses on Heart Tissue

Short duration voltage pulses such as those described herein have at least three different effects on myocardial tissues, depending on the local strength of the applied field or voltage gradient. Field strengths above 500V/cm damage myocytes and can be lethal when applied multiple times. Tissue stunning can occur with single high-voltage pulses having voltage gradients above 500V/cm, with myocardial tissue being unresponsive to stimulation for more than 30 seconds following the delivered pulse. Stunning can also occur in myocardial tissue exposed to multiple applied pulses producing gradients of 100-500 V/cm in the affected tissue. When a DC voltage pulse is used with the pulse duration of about 0.1 msec, tissue exposed to stimulation strengths of from about 10 to 100 VI cm can be stimulated (paced) by the applied pulse. If only atrial tissue is so stimulated, such stimulation typically is not a safety issue, and may provide diagnostic information to the user of this ablation technology. However, if the field stimulation extends to the ventricle, such stimulation can induce ventricular tachycardia or even ventricular fibrillation. This potential safety issue can be addressed either by applying the voltage pulse synchronously with ventricular contraction (during the QRS complex of the ECG) by applying a sequence of higher frequency pulses instead of a single DC pulse, or by applying a pulsed RF waveform.

Tissue Heating

When ablating tissue with high voltages, the pulse sequence is usually designed to result in peak tissue temperatures of less than about 50° C. so that little or no thermally-induced tissue ablation occurs. Often, it is also useful to avoid creating tissue temperatures that exceed about 65° C., which can coagulate the tissue and result in geometrical changes to the tissue structures both on a microscopic and visual scale. Coagulated tissue is typically more thrombogenic than tissue containing cells lethally injured by high-voltage pulses. Furthermore, healing is generally expected to proceed more rapidly because the non-cellular structure of the heart is not modified by the voltage structure and some blood flow through the tissue would be maintained. The pulse sequences generally described herein do not heat the ablated tissues significantly, according to tome embodiments. Even with the most aggressive pulse sequences described (highest voltages, longest pulse durations, and most pulse numbers), the total amount of heating is less than that typically provided by one second of RF ablation and less than 1% of the energy needed to produce a thermally-based ablation lesion.

The lack of clear changes to the tissue appearance can result in errors of producing overlapping lesions, which is commonly required for AF therapies. One method which enables visualization of lesions involves creating a local thermal injury after providing the fatal high-voltage pulse sequence through the application electrodes. For example, it is possible to create such local visually apparent lesions with a short pulse of RF power delivered for 3 seconds or less. For short applications of power to the tissues, the lesion volume typically is determined by the tissues directly heated and thermal expansion of the lesion is minimized. Optionally, high-voltage pulses with longer pulse durations can be delivered to the tissues to provide a similar tissue heating.

Related Suction Stabilized Bipolar Embodiments

Aspects of high voltage pulse ablation as described herein are well suited for use in suction stabilized bipolar ablation systems and methods. For example, suction stabilized bipolar techniques as described in U.S. Provisional Patent Application No. 61/456,918, filed Nov. 12, 2010, incorporated herein by reference, can be used to administer exemplary high voltage pulse ablations. Optionally, such treatments may involve the use of temperature sensors. In some cases, temperature sensing techniques can be used in conjunction with a marking process.

Marking Techniques

Following the application of various high voltage pulse or radiofrequency energy ablation treatments, it may be difficult to directly visualize or distinguish a lesion generated by the treatment. For example, the tissue surface may not be heated sufficiently to create a visible mark. Hence, a surgeon may not be able to see the lesion with the unaided eye, without assistance from a magnifying or other vision-enhancing optical device. In these and other instances, it may be desirable or helpful to create a mark or indicia on the tissue surface which corresponds to the lesion.

In some cases, administration of radiofrequency energy can be used to form such markings. For example, radiofrequency energy can be applied so as to heat the tissue surface to a temperature of about 60° C. or greater, which results in a visible mark that can be easily seen by a surgeon or operator. In some cases, certain high voltage pulse regimens can be used to form such markings by purposefully heating the tissue. For example, such heating can be achieved by increasing the magnitude of the voltage pulse, or by increasing the width of the voltage pulse, thus forming a visible mark on the tissue surface. The delivered energy requirement to locally increase temperatures to 60° C. so as to create a visible mark varies by electrode configuration but is typically about 10 Joules/cm of electrode length. The energy can be delivered with several pulses using temperature monitoring to the energy delivered. Since only a surface mark is desired, the thermal marking energy should be delivered in less than three seconds. Heating the tissue to temperatures higher than 90° C. should be avoided, since such temperatures can dry out the tissue and interfere with any subsequent ablation attempts.

Accordingly, either a high voltage pulse ablation protocol or a radiofrequency energy ablation protocol may be performed to create a lesion in the tissue, and either a high voltage pulse ablation protocol or a radiofrequency energy ablation protocol may be performed to create a mark on the tissue.

In some cases, marking may act to dry out the outer surface of the tissue, making it more resistive, and thus interfere with formation of the lesion.

In some cases, high voltage gradients can be used to make the transmural lesion, and even higher voltage gradients can be used to make the surface mark. Relatedly, the high voltage gradients used to make the transmural lesion may in some cases be more reliable than the even higher voltage gradients used to make the surface mark. According to some embodiments, it may be easier to increase pulse width rather than pulse voltage to thermally heat the tissue for marking. Higher voltages may provide more assured irreversible cellular damage, independent of thermal effects.

According to some embodiments, a tissue surface mark can have a depth within a range from about 0.5 mm to about 3.0 mm. In some cases, a tissue surface mark may be about 1 mm deep.

Individual system elements or aspects of a tissue treatment computer system may be implemented in a separated or more integrated manner. In some embodiments, treatment systems, which may include computer systems, also include software elements, for example located within a working memory of a memory, including an operating system and other code, such as a program designed to implement method embodiments of the present invention. In some cases, software modules implementing the functionality of the methods as described herein, may be stored in a storage subsystem. It is appreciated that systems can be configured to carry out various method aspects described herein. Each of the devices or modules of the present invention can include software modules on a computer readable medium that is processed by a processor, hardware modules, or any combination thereof. Any of a variety of commonly used platforms, such as Windows, Macintosh, and Unix, along with any of a variety of commonly used programming languages, such as C or C++, may be used to implement embodiments of the present invention. In some cases, tissue treatment systems include FDA validated operating systems or software/hardware modules suitable for use in medical devices. Tissue treatment systems can also include multiple operating systems. For example, a tissue treatment system can include a FDA validated operating system for safety critical operations performed by the treatment system, such as data input, power control, diagnostic procedures, recording, decision making, and the like. A tissue treatment system can also include a non-validated operating system for less critical operations. In some embodiments, a computer system can be in integrated into a tissue treatment system, and in some embodiments, a computer system can be separate from, but in connectivity with, a tissue treatment system. It will be apparent to those skilled in the art that substantial variations may be used in accordance with any specific requirements. For example, customized hardware might also be used and/or particular elements might be implemented in hardware, software (including portable software, such as applets), or both. Further, connection to other computing devices such as network input/output devices may be employed. Relatedly, any of the hardware and software components discussed herein can be integrated with or configured to interface with other medical treatment or information systems used at other locations.

While exemplary embodiments have been described in some detail, by way of example and for clarity of understanding, those of skill in the art will recognize that a variety of modification, adaptations, and changes may be employed. Hence, the scope of the present invention should be limited solely by the claims.

I claim:

1. A method of ablating a tissue, the method comprising:
compressing a target tissue including myocytes between a first jaw comprising a first electrode and a second jaw comprising a second electrode;
non-thermally ablating the myocytes by delivering voltage pulses at or above 500 volts to the target tissue via at least one of the first electrode and the second electrode;
wherein delivering voltage pulses to the target tissue via the at least one of the first electrode and the second electrode comprises delivering about 5-50 pulses at about 1500-3000 Volts with pulse durations of about 0.02-0.1 milliseconds over a time interval of about 1-60 seconds.

2. The method of claim 1, wherein delivering voltage pulses to the target tissue via the at least one of the first electrode and the second electrode comprises applying a voltage pulse regimen to the target tissue via the at least one of the first electrode and the second electrode.

3. The method of claim 2,
wherein the target tissue comprises a plurality of myocardial cells; and
wherein the voltage pulse regimen is sufficient to irreversibly damage the plurality of myocardial cells.

4. The method of claim 1, wherein delivering voltage pulses to the target tissue via the at least one of the first electrode and the second electrode comprises applying at least one of bipolar energy and monopolar energy to the target tissue via the at least one of the first electrode and the second electrode.

5. The method of claim 1, wherein compressing the target tissue comprises operating an actuator to move at least one of the first jaw and the second jaw to close the first jaw and the second jaw.

6. The method of claim 1, wherein compressing the target tissue comprises closing the first jaw and the second jaw so that the first jaw and the second jaw are separated by less than about 5 millimeters.

7. The method of claim 1, further comprising automatically individually adjusting the voltage pulses delivered via the at least one of the first electrode and the second electrode to accommodate variable tissue thicknesses between the first electrode and the second electrode, wherein automatically individually adjusting includes adjusting the voltage pulses to deliver voltage pulses above about 500 Volts per centimeter.

8. The method of claim 7, wherein delivering voltage pulses to the target tissue via the at least one of the first electrode and the second electrode comprises delivering the voltage pulses to the target tissue synchronously with ventricular contraction.

9. The method of claim 1, further comprising adhering at least one of the first electrode and the second electrode to the target tissue by applying suction.

10. The method of claim 1, further comprising creating a mark or indicia on a surface of the target tissue corresponding to a lesion.

* * * * *